US012778687B2

(12) United States Patent
Katsuyama et al.

(10) Patent No.: US 12,778,687 B2
(45) Date of Patent: Nov. 3, 2026

(54) CONTROL APPARATUS, MEDICAL CENTRAL CONTROL SYSTEM, AND SURGERY-RELATED INFORMATION DISPLAY METHOD

(71) Applicant: OLYMPUS CORPORATION, Tokyo (JP)

(72) Inventors: Takayuki Katsuyama, Tokyo (JP); Kiyoshi Sekiguchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 529 days.

(21) Appl. No.: 18/096,070

(22) Filed: Jan. 12, 2023

(65) Prior Publication Data

US 2023/0149100 A1 May 18, 2023

Related U.S. Application Data

(63) Continuation of application No. PCT/JP2020/027693, filed on Jul. 16, 2020.

(51) Int. Cl.
*A61B 34/00* (2016.01)
*A61B 90/00* (2016.01)

(52) U.S. Cl.
CPC .............. *A61B 34/25* (2016.02); *A61B 90/37* (2016.02); *A61B 2034/256* (2016.02); *A61B 2034/258* (2016.02)

(58) Field of Classification Search
CPC ... A61B 34/25; A61B 90/37; A61B 2034/258; A61B 2034/252; A61B 34/10
See application file for complete search history.

(56) References Cited

U.S. PATENT DOCUMENTS

| | | | | |
|---|---|---|---|---|
| 2007/0174090 | A1 | 7/2007 | Friedlander et al. | |
| 2011/0263980 | A1* | 10/2011 | Mills | G16H 70/20 715/764 |
| 2017/0035287 | A1* | 2/2017 | Ren | A61B 3/0058 |
| 2018/0368930 | A1* | 12/2018 | Esterberg | G06T 19/003 |
| 2019/0090954 | A1 | 3/2019 | Kotian et al. | |
| 2019/0201143 | A1* | 7/2019 | Shelton, IV | A61B 34/25 |
| 2020/0129044 | A1* | 4/2020 | Yamaoka | A61B 1/00149 |
| 2020/0170710 | A1* | 6/2020 | Rus | G16H 20/40 |

FOREIGN PATENT DOCUMENTS

| | | | |
|---|---|---|---|
| EP | 3474285 | A2 | 4/2019 |
| JP | H07132121 | A | 5/1995 |
| JP | 2003284690 | A | 10/2003 |

(Continued)

OTHER PUBLICATIONS

International Search Report dated Oct. 6, 2020 issued in PCT/JP2020/027693.

*Primary Examiner* — Carl H Layno
*Assistant Examiner* — Bryan McAllister Lee
(74) *Attorney, Agent, or Firm* — Scully, Scott, Murphy & Presser, P.C.

(57) ABSTRACT

A control apparatus includes a processor. The processor selects one scene of a plurality of scenes of a predetermined surgical operation based on user input, changes settings of a surgical apparatus according to the scene selected when each scene is selected, selects surgery-related information according to the scene selected, and displays the surgery-related information on a display unit.

20 Claims, 28 Drawing Sheets

(56) References Cited

FOREIGN PATENT DOCUMENTS

| | | | |
|---|---|---|---|
| JP | 2003330597 | A | 11/2003 |
| JP | 2015197757 | A | 11/2015 |
| JP | 2019185726 | A | 10/2019 |
| WO | 2014196292 | A1 | 12/2014 |
| WO | 2019111512 | A1 | 6/2019 |

* cited by examiner

SCENE SELECTION SETTING BUTTON IS PRESSED ON OPERATING PANEL.

DESIRED SCENE (SCENE 1) IS SELECTED.

WHEN SCENE SETTING IS COMPLETE, SCENE SET ON TOUCH PANEL BECOMES SELECTABLE.

FIG. 5

| PROCEDURE | SCENE | DETAILS OF SETTINGS |
|---|---|---|
| CHOLECYSTECTOMY | 1. PREPARATION | ・[MOVIE] HANDPIECE ASSEMBLY<br>-CHAPTER NAME: ASSEMBLY<br>-TIMING: DURING SCENE SELECTION<br>・[DEVICE SETTING] ROOM LIGHT OFF<br>・[DEVICE SETTING] SHADOWLESS LIGHTS ON |
| | 2. ENDOSCOPE INSERTION | ・[DEVICE SETTING] VIDEO SYSTEM CENTER<br>- WHITE BALANCE ADJUSTMENT<br>・[INSTRUCTION MANUAL] INSTRUCTION MANUAL FOR VIDEO SYSTEM CENTER<br>-PAGE TO BE DISPLAYED: PAGE 70 (HOW TO ACQUIRE WHITE BALANCE)<br>-TIMING: DURING SCENE SELECTION |
| | 3. START OF HANDPIECE USE | ・[MOVIE] HOW TO USE HANDPIECE<br>-CHAPTER NAME: HOW TO USE<br>-TIMING: DURING SCENE SELECTION<br>・[DEVICE SETTING] 100 W WHEN ELECTROCAUTERY IS SET UP |
| | 4. END OF SURGICAL OPERATION | ・[INSTRUCTION MANUAL] CLEANUP METHOD<br>-PAGE TO BE DISPLAYED: PAGE 120<br>-TIMING: DURING SCENE SELECTION |

DESIRED SCENE IS SELECTED USING TOUCH PANEL.

WHEN LIST OF SETTING DETAILS IS DISPLAYED, ENTER IS PRESSED IF THERE IS NO PROBLEM.

AFTER "1. PREPARATION" SCENE IS RUN, MOVIE SET ON OPERATING PANEL IS DISPLAYED (PLAYED).

AFTER SCENE OF "2. ENDOSCOPE INSERTION" IS RUN, INSTRUCTION MANUAL PAGE SET ON OPERATING PANEL IS DISPLAYED.

FIG. 7

| MOVIE/INSTRUCTION MANUAL USER WANTS TO VIEW | PROCEDURE | SEARCH CONDITIONS A FOR REFERENCE MATERIAL/MOVIE | SEARCH CONDITIONS B FOR REFERENCE MATERIAL/MOVIE |
|---|---|---|---|
| HANDPIECE ASSEMBLY MOVIE<br><br>CHAPTER NAME: ASSEMBLY | CHOLECYSTECTOMY | a. SCENE TO BE RUN FIRST*<br><br>*WHICH CORRESPONDS TO "PREPARATION" SCENE IN FIG. 5 | a. TO SEARCH FOR MOVIE AND CHAPTER OF HANDPIECE ASSEMBLY METHOD REFERRED TO IN PAST IN SCENE TO BE RUN FIRST AND SET SEARCH RESULTS FOR SCENE,<br>OR<br>c. TO TAKE PICTURE OF HANDPIECE USING CAMERA OR READ BARCODE, RFID, OR THE LIKE, AND IDENTIFY HANDPIECE TO BE USED AND MOVIE. ALSO, SET CHAPTER CARRYING ASSEMBLY METHOD OF HANDPIECEFOR SCENE BASED ON SCENE ORDER. |
| INSTRUCTION MANUAL FOR VIDEO SYSTEM CENTER<br><br>PAGE TO BE DISPLAYED: PAGE 70 | | b. SCENE IN WHICH DEVICE SETTINGS INCLUDE WHITE BALANCE ADJUSTMENT | d. TO DISCRIMINATE INSTRUCTION MANUAL FOR VIDEO SYSTEM CENTER BASED ON DEVICE TO BE USED AND SET PAGE NUMBER OF PAGE DESCRIBING HOW TO ACQUIRE WHITE BALANCE BASED ON SETTING DETAILS. |
| MOVIE OF HOW TO USE HANDPIECE (DISPLAYED BEFORE USE)<br><br>CHAPTER NAME: HOW TO USE | | a, b. SCENE IN WHICH DEVICE SETTINGS INCLUDE ELECTROCAUTERY OUTPUT VALUE (ELECTROCAUTERY OUTPUT IS SET FOR FIRST TIME FOR THIS SCENE) | b. TO DISCRIMINATE HANDPIECE TO BE USED AND CORRESPONDING MOVIE BASED ON DEVICE (ELECTROCAUTERY) TO BE USED AND PROCEDURE NAME OF CHOLECYSTECTOMY. ALSO, TO SET HOW-TO-USE-HANDPIECE CHAPTER FOR SCENE (HOW-TO-USE-HANDPIECE CHAPTER IS DISCRIMINATED SINCE ELECTROCAUTERY OUTPUT VALUE IS SET FOR FIRST TIME FOR THIS SCENE). |
| CLEANUP METHOD FOR DEVICES, INSTRUCTION MANUAL FOR STORAGE SPACE<br><br>PAGE TO BE DISPLAYED: PAGE 120 | | a. FINAL SCENE | d. RESPECTIVE INSTRUCTION MANUALS FOR EQUIPMENT AND MATERIALS ARE SET BASED ON FINAL SCENE AND EQUIPMENT AND MATERIALS USED, AND PAGE CARRYING CLEANUP METHOD FOR EQUIPMENT AND MATERIALS IS SET BASED ON FINAL SCENE. |

FIG. 13

| PROCEDURE | SCENE | REGISTRATION CONTENTS |
|---|---|---|
| GENERAL CHOLECYSTECTOMY PROCEDURE (USE STANDARD CAVITY MODE) | ABDOMINAL PRESSURE SETTING (STANDARD CAVITY MODE) | •[DEVICE SETTING] SET PRESSURE OF INSUFFLATION DEVICE: 15 mmHg<br>•[INSTRUCTION MANUAL] INSTRUCTION MANUAL FOR PNEUMOPERITONEUM DEVICE<br>-PAGE TO BE DISPLAYED: PAGE 70 (CAUTIONS IN FEEDING GAS IN STANDARD CAVITY MODE)<br>-TIMING: UPON PRESS OF START FEEDING GAS BUTTON OF INSUFFLATION DEVICE |
| PEDIATRIC CHOLECYSTECTOMY (USE SMALL CAVITY MODE) | ABDOMINAL PRESSURE SETTING (SMALL CAVITY MODE) | •[DEVICE SETTING] SET PRESSURE OF INSUFFLATION DEVICE: 12 mmHg<br>•[INSTRUCTION MANUAL] INSTRUCTION MANUAL FOR PNEUMOPERITONEUM DEVICE<br>-PAGE TO BE DISPLAYED: PAGE 75 (CAUTIONS IN FEEDING GAS IN STANDARD CAVITY MODE)<br>-TIMING: UPON PRESS OF START FEEDING GAS BUTTON OF INSUFFLATION DEVICE |

REFERENCE MANUAL IS DISPLAYED
(CAUTIONS IN FEEDING GAS IN SMALL CAVITY MODE)

FIG. 16

| MOVIE/INSTRUCTION MANUAL USER WANTS TO VIEW | PROCEDURE | SEARCH CONDITIONS A FOR REFERENCE MATERIAL /MOVIE | SEARCH CONDITIONS B FOR REFERENCE MATERIAL/MOVIE |
|---|---|---|---|
| INSTRUCTION MANUAL CONTAINING CAUTIONS IN STANDARD CAVITY MODE<br><br>PAGE TO BE DISPLAYED: PAGE 70 | GENERAL CHOLECYSTECTOMY | b. SCENE IN WHICH DEVICE SETTINGS INCLUDE START OF GAS-FEEDING | b. TO DISCRIMINATE REFERENCE MATERIAL FOR INSUFFLATION DEVICE BASED ON PROCEDURE AND SCENE SETTING DETAILS (START OF GAS FEEDING). ALSO, TO SET PAGE NUMBER CONTAINING CAUTIONS IN FEEDING GAS IN STANDARD CAVITY MODE FOR SCENE BASED ON PROCEDURE AND SCENE SETTING DETAILS<br>(SET PRESSURE OF INSUFFLATION DEVICE) |
| INSTRUCTION MANUAL CONTAINING CAUTIONS IN SMALL CAVITY MODE<br><br>PAGE TO BE DISPLAYED: PAGE 75 | PEDIATRIC CHOLECYSTECTOMY | b. SCENE IN WHICH DEVICE SETTINGS INCLUDE START OF GAS-FEEDING | d. TO DISCRIMINATE REFERENCE MATERIAL FOR INSUFFLATION DEVICE BASED ON PROCEDURE AND SCENE SETTING DETAILS (START OF GAS FEEDING). ALSO, TO SET PAGE NUMBER CONTAINING CAUTIONS IN FEEDING GAS IN SMALL CAVITY MODE FOR SCENE BASED ON PROCEDURE AND SCENE SETTING DETAILS<br>(SET PRESSURE OF INSUFFLATION DEVICE) |

FIG. 20

| PROCEDURE | SCENE | REGISTRATION CONTENTS |
| --- | --- | --- |
| CHOLECYSTECTOMY | ENDOSCOPE INSERTION | •[DEVICE SETTING] ELECTROCAUTERY BIPOLAR 80 W<br>•[INSTRUCTION MANUAL] INSTRUCTION MANUAL FOR ELECTROCAUTERY<br>-PAGE TO BE DISPLAYED: PAGE 40 (DEALING WITH CHOLECYSTIC HANDPIECE OUTPUT ERROR)<br>-TIMING: UPON OCCURRENCE OF HANDPIECE ERROR |
| GASTRECTOMY | ENDOSCOPE INSERTION | •[DEVICE SETTING] ELECTROCAUTERY BIPOLAR 60 W<br>•[INSTRUCTION MANUAL] INSTRUCTION MANUAL FOR ELECTROCAUTERY<br>-PAGE TO BE DISPLAYED: PAGE 45 (DEALING WITH GASTRIC HANDPIECE OUTPUT ERROR)<br>-TIMING: UPON OCCURRENCE OF HANDPIECE ERROR |

FIG. 21
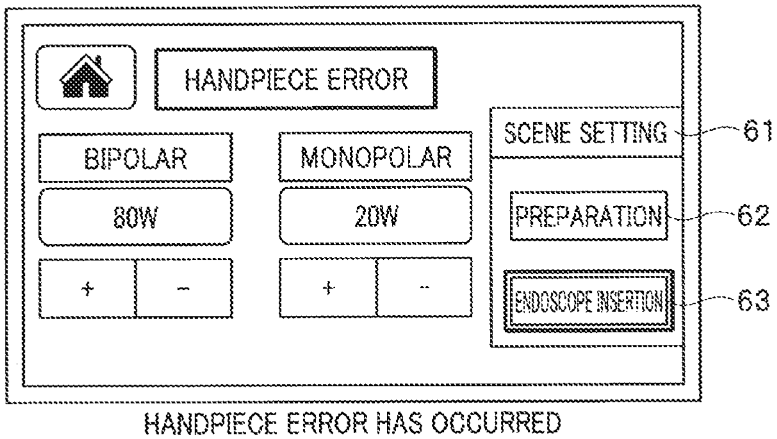
HANDPIECE ERROR HAS OCCURRED
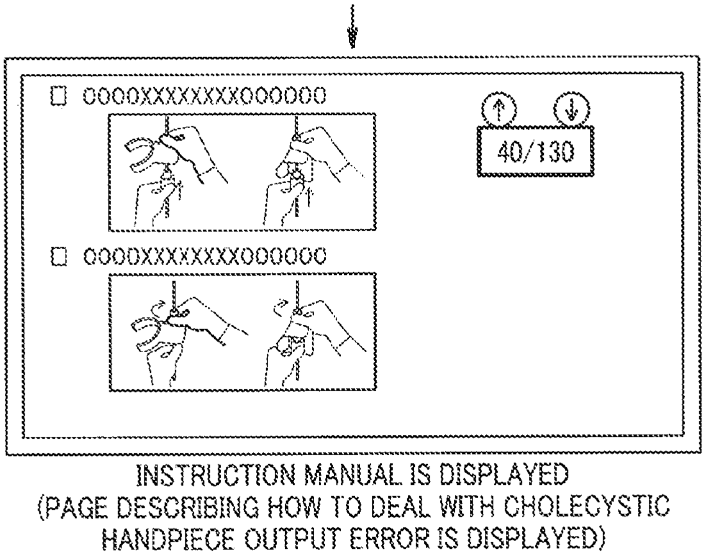
INSTRUCTION MANUAL IS DISPLAYED
(PAGE DESCRIBING HOW TO DEAL WITH CHOLECYSTIC HANDPIECE OUTPUT ERROR IS DISPLAYED)

FIG. 23

| MOVIE/INSTRUCTION MANUAL USER WANTS TO VIEW | PROCEDURE | SEARCH CONDITIONS A FOR REFERENCE MATERIAL /MOVIE | SEARCH CONDITIONS B FOR REFERENCE MATERIAL/MOVIE |
|---|---|---|---|
| INSTRUCTION MANUAL DESCRIBING HOW TO DEAL WITH CHOLECYSTIC HANDPIECE OUTPUT ERROR<br><br>PAGE TO BE DISPLAYED: PAGE 40 | CHOLECYSTECTOMY | a, b. SCENE IN WHICH DEVICE SETTINGS INCLUDE ELECTROCAUTERY OUTPUT VALUE | b. TO DISCRIMINATE REFERENCE MATERIAL FOR CHOLECYSTECTOMIC HANDPIECE OUTPUT ERROR BASED ON PROCEDURE (CHOLECYSTECTOMY) AND DEVICE USED.<br>ALSO, TO SET PAGE NUMBER DESCRIBING HOW TO DEAL WITH CHOLECYSTIC HANDPIECE OUTPUT ERROR FOR SCENE, BASED ON SETTING DETAILS (IN CASE OF HANDPIECE OUTPUT ERROR) |
| INSTRUCTION MANUAL DESCRIBING HOW TO DEAL WITH GASTRIC HANDPIECE OUTPUT ERROR<br><br>PAGE TO BE DISPLAYED: PAGE 45 | GASTRECTOMY | a, b. SCENE IN WHICH DEVICE SETTINGS INCLUDE ELECTROCAUTERY OUTPUT VALUE | b. TO DISCRIMINATE REFERENCE MATERIAL FOR GASTRECTOMIC HANDPIECE OUTPUT ERROR BASED ON PROCEDURE (GASTRECTOMY) AND DEVICE USED.<br>ALSO, TO SET PAGE NUMBER DESCRIBING HOW TO DEAL WITH GASTRIC HANDPIECE OUTPUT ERROR FOR SCENE, BASED ON SETTING DETAILS (IN CASE OF HANDPIECE OUTPUT ERROR) |

CONTROL APPARATUS, MEDICAL CENTRAL CONTROL SYSTEM, AND SURGERY-RELATED INFORMATION DISPLAY METHOD

CROSS REFERENCE TO RELATED APPLICATION

This application is a continuation application of PCT/JP2020/027693 filed on Jul. 16, 2020, the entire contents of which are incorporated herein by this reference.

BACKGROUND OF THE INVENTION

1. Field of the Invention

The present invention relates to a control apparatus, a medical central control system, and a surgery-related information display method, and in particular, to a control apparatus configured to control a plurality of controlled devices, a medical central control system, and a surgery-related information display method.

2. Description of the Related Art

Conventionally, various types of medical devices and various types of non-medical devices have been installed in operating rooms. The various types of devices are various devices including shadowless lights, endoscope apparatus, and insufflation devices. A system controller serving as a central control apparatus communicates with the various types of devices, and establishes set values and centrally controls the various types of devices.

When an operating panel is connected to the system controller and a surgical operation is started, surgical staff including an operating surgeon, a scopist, and nurses can give operation commands to desired devices as well as establish and change various set values by operating the operating panel.

Operation of each device includes instructions to execute or stop functions of the device as well as function settings, and the surgical staff including the operating surgeon, scopist, and nurses operate each device directly or perform a desired operation by displaying an operation screen on the operating panel.

Such a central control apparatus has a scene selection function of collectively setting (states of) various types of devices according to the progress of a surgical operation. The scene selection function normally involves making only settings for various types of devices according to the progress of a surgical operation.

Incidentally, if, for example, a handpiece is assembled during a surgical operation, the surgical staff needs to learn how to assemble the handpiece, in advance using an instruction manual or video.

SUMMARY OF THE INVENTION

A control apparatus according to one aspect of the present invention includes a processor, wherein: the processor selects one scene of a plurality of scenes of a predetermined surgical operation based on user input; changes settings of a surgical apparatus according to the scene selected when each scene is selected; selects surgery-related information according to the scene selected; and displays the surgery-related information on a display unit.

A medical central control system according to another aspect of the present invention includes: a plurality of medical devices; and a control apparatus that includes a processor and controls the plurality of medical devices, wherein the processor selects one scene of a plurality of scenes of a predetermined surgical operation based on user input, changes settings of the medical devices according to the scene selected when each scene is selected, selects surgery-related information according to the scene selected, and displays the surgery-related information on a display unit.

A surgery-related information display method according to another aspect of the present invention includes selecting one scene of a plurality of scenes of a predetermined surgical operation based on user input; changes settings of the medical devices according to the scene selected when each scene is selected, selecting surgery-related information according to the scene selected, and displaying the surgery-related information.

BRIEF DESCRIPTION OF THE DRAWINGS

FIG. 5 is a diagram showing an example of scene setting details related to cholecystectomy procedures;

FIG. 7 is a diagram for explaining an example of search conditions for an instruction manual or a movie which a user wants to view;

FIG. 13 is a diagram showing an example of registration contents set for each procedure and scene;

FIG. 16 is a diagram showing search conditions for a reference material to be set;

FIG. 20 is a diagram showing an example of registration contents set for each procedure and scene;

FIG. 21 is a diagram for explaining an example of a display screen appearing when a handpiece error occurs;

FIG. 23 is a diagram showing search conditions for a reference material to be set;

DETAILED DESCRIPTION OF THE PREFERRED EMBODIMENTS

Embodiments of the present invention will be described below using the drawings.

First Embodiment (Configuration of Surgery System)

Figure 1:
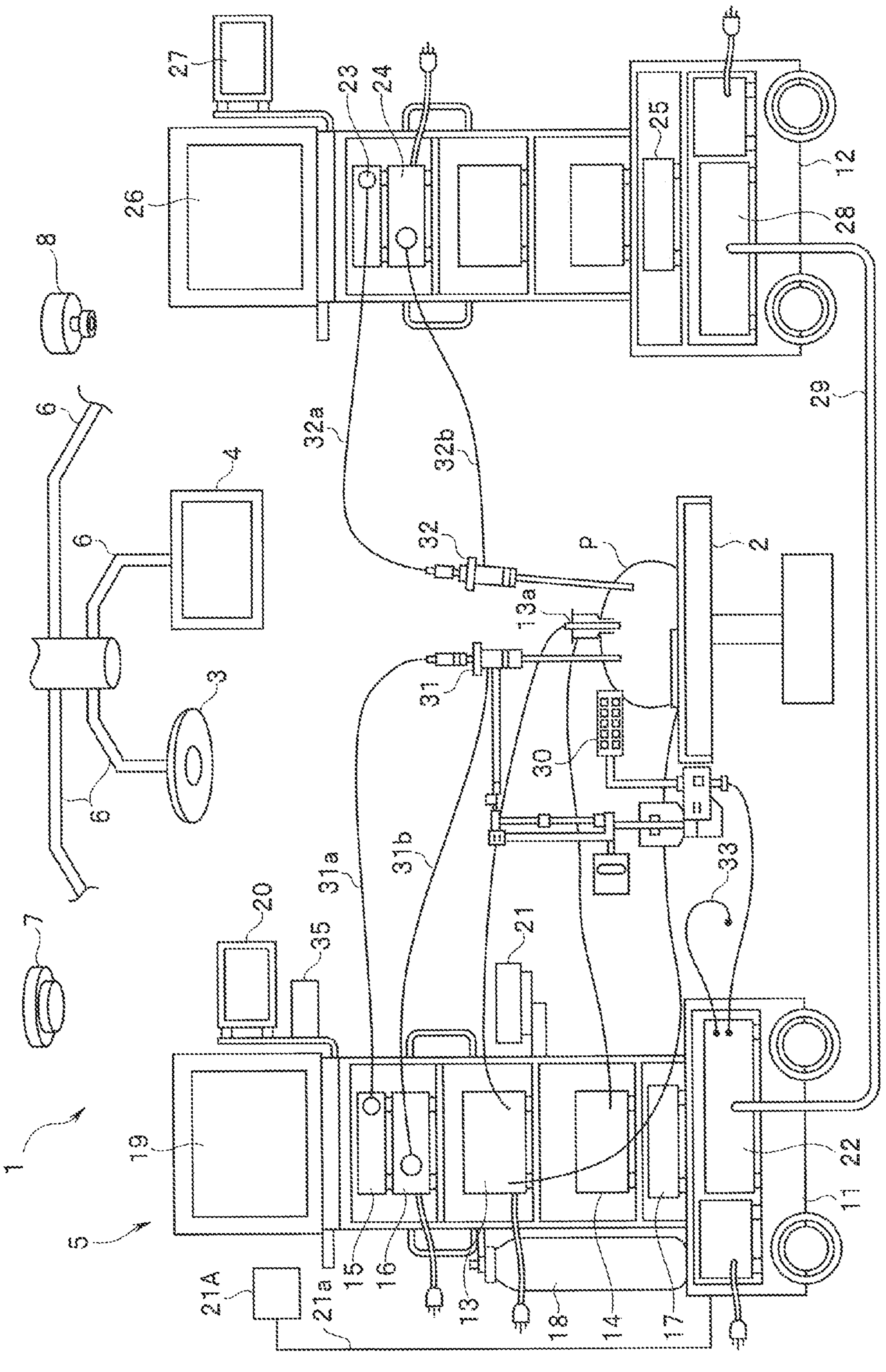
FIG. 1 is a configuration diagram showing a configuration of a surgery system according to a first embodiment of the present invention.

First, an overall configuration of a surgery system placed in an operating room will be described using FIG. 1. FIG. 1 is a configuration diagram showing a configuration of a surgery system according to a first embodiment of the present invention. The surgery system includes a plurality of medical devices such as endoscopes and a plurality of non-medical devices such as shadowless lights.

As shown in FIG. 1, a surgical table 2 on which a patient P lies down, a plurality of shadowless lights 3, a display device 4, and a medical system 5 are placed in the operating room. The medical system 5 includes a first cart 11 and a second cart 12. The plurality of shadowless lights 3 and the display device 4 are fixed to a ceiling of the operating room by arms 6. Furthermore, a room light 7 is installed on the ceiling of the operating room. Besides, a surgical field camera 8 and a non-illustrated room camera are installed in the operating room.

Medical devices, which are controlled devices, as well as a gas cylinder 18 filled with carbon dioxide are placed on the first cart 11, where the medical devices include an electrocautery device 13, an insufflation device 14, a video processor 15, a light source device 16, and a recorder 17 for recording. The video processor 15 is connected to a first endoscope 31 via a camera cable 31*a*.

The light source device 16 is connected to the first endoscope 31 via a light guide cable 31*b*. A display device 19, a first central display panel 20, an operating panel 21, and the like are also placed on the first cart 11. The display device 19 is, for example, a TV monitor that displays endoscopic images and the like.

The recorder 17 is a recording device including a mass-storage device such as a hard disk drive.

The central display panel 20 is display means capable of selectively displaying any data on a surgical operation. The operating panel 21 is made up, for example, of a display unit such as a liquid crystal display and a touch panel provided integrally on the display unit, and makes up a central operating device operated by a nurse or the like located in a non-sterilized area.

Furthermore, a system controller 22, which is a central control apparatus, is placed on the first cart 11. The system controller 22 is connected with the plurality of shadowless lights 3, the room light 7, the electrocautery device 13, the insufflation device 14, the video processor 15, the light source device 16, the recorder 17, and the like described above via non-illustrated communications lines. Furthermore, the system controller 22 is designed to be connectable with a headset microphone 33, capable of recognizing voice inputted through the microphone 33, and capable of controlling various devices by surgeon's voice.

The system controller 22 is also connected via a cable 21*a* with a second operating panel 21A installed on a wall of the operating room and the nurse and the like located in the non-sterilized area can operate various devices also via the operating panel 21A.

An RFID (radio frequency identification) terminal 35 capable of wirelessly reading/writing individual ID information on items using ID tags embedded in the first endoscope 31, a treatment instrument 13*a* connected to the electrocautery device 13, and the like is provided on the first cart 11.

On the other hand, a video processor 23, a light source device 24, an image processing apparatus 25, a display device 26, and a central display panel 27 are placed on the second cart 12. The video processor 23 is connected to a second endoscope 32 via a camera cable 32*a*. The light source device 24 is connected to the second endoscope 32 via a light guide cable 32*b*.

The display device 26 displays endoscopic images and the like captured by the video processor 23. The central display panel 27 can selectively display any data on a surgical operation.

The video processor 23, the light source device 24, the image processing apparatus 25, and the like are connected to a relay unit 28 placed on the second cart 12, via non-illustrated communications lines. The relay unit 28 in turn is connected to the system controller 22 mounted on the first cart 11 described earlier via a relay cable 29.

This allows the system controller 22 to centrally control the video processor 23, the light source device 24, the image processing apparatus 25, and the like mounted on the second cart 12; the electrocautery device 13, the insufflation device 14, the video processor 15, the light source device 16, the recorder 17, and the like mounted on the first cart 11; and the plurality of shadowless lights 3, the plurality of display devices 4, the room light 7, and the like.

Therefore, the system controller 22 is designed to be able to display setting screens for setting states, operating switches, and the like on the liquid crystal displays of the operating panels 21 and 21A of the connected devices when communications are being conducted between the system controller 22 and the above-mentioned devices. Furthermore, the system controller 22 is designed to accept an operator input such as a set-value change when a desired operating switch is touched and a predetermined region on a touch panel is operated.

A remote controller 30 is a second central operating device operated by an operating surgeon or the like located in a sterilized area, and allows other devices with which communications have been established to be operated via the system controller 22.

An infrared communications port (not shown), which is communications means, is attached to the system controller 22. The infrared communications port is provided in an easy place to emit infrared radiation, such as near the display device 19, and connected with the system controller 22 via a cable.

(Configuration of System Controller 22)

Figure 2:
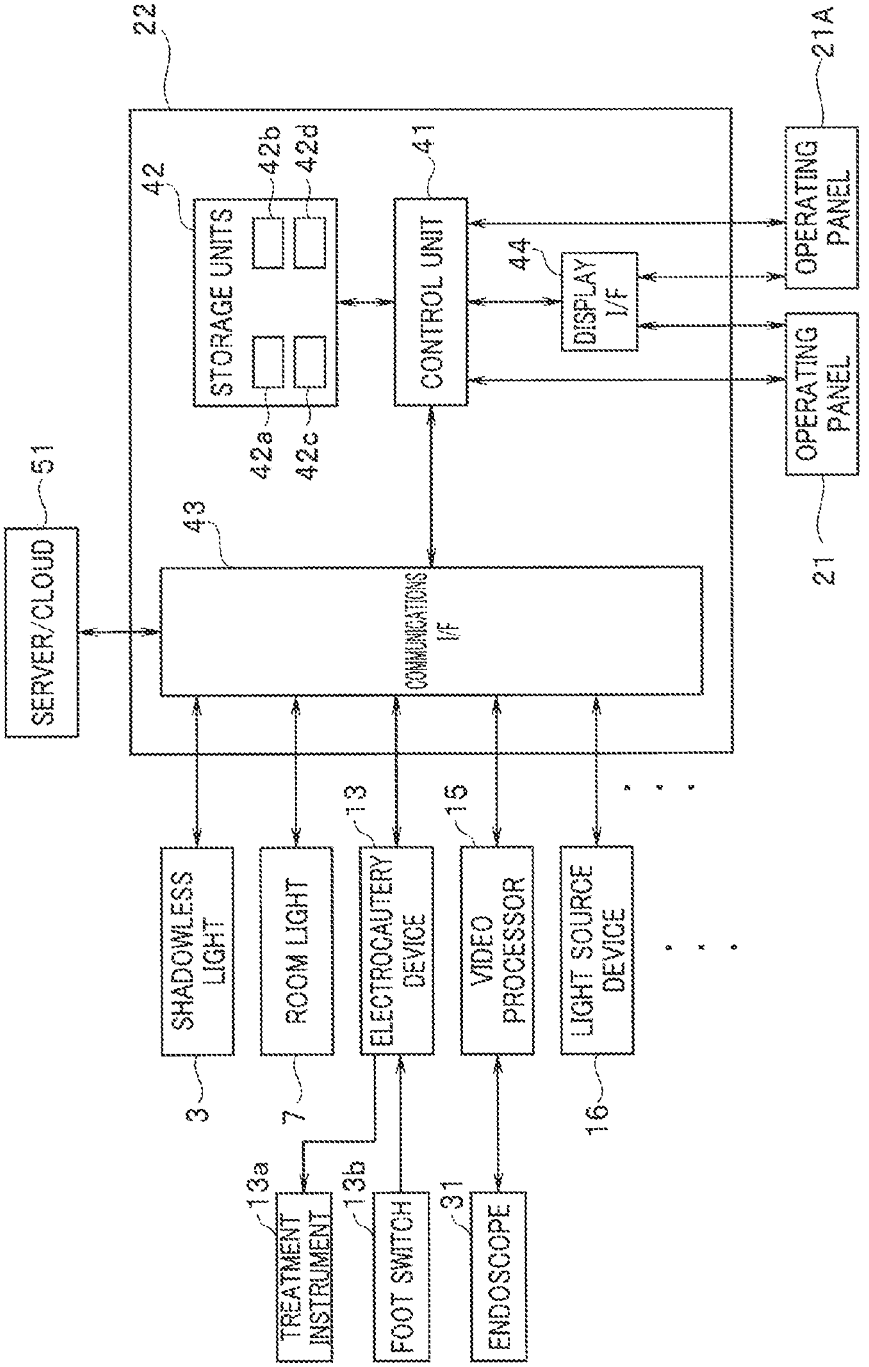
FIG. 2 is a block diagram showing a configuration of a system controller.

FIG. 2 is a block diagram showing a configuration of the system controller.

The system controller 22 includes a control unit 41, a storage device 42, a communications interface (hereinafter abbreviated to a communications I/F) 43, and a display interface (hereinafter abbreviated to a display I/F) 44.

The control unit 41 can be configured as a processor equipped with a central processing unit (hereinafter referred to as a CPU), a ROM, a RAM, and the like, and various functions of the system controller 22 are implemented when the CPU executes relevant software programs read out of the ROM. The processor here may, for example, either implement functions of various components on separate pieces of hardware or implement part of the various components on an integral piece of hardware. For example, the processor includes hardware, which can include at least one of a circuit that processes digital signals or a circuit that processes analog signals. As the processor, various types of processors such as a DSP (digital signal processor) are available for use besides the central processing unit (CPU). Besides, the processor may be a hardware circuit based on an ASIC (application specific integrated circuit) or an FPGA (field programmable gate Array).

The storage device 42 is a nonvolatile rewritable storage device such as a flash memory or a hard disk drive. The storage device 42 also stores software programs for various functions of the system controller 22, and the software programs can be read out and executed by the CPU of the control unit 41.

The storage device 42 includes a program storage unit 42*a* configured to store software programs for various functions, where the software programs include programs used to set a plurality of devices for each scene, display information on the most suitable reference material for each scene, and the like described later.

The software programs stored in the program storage unit 42*a* include not only a control program configured to control operations of various devices included in the surgery system 1, but also a collective setting program used to make device settings collectively for each scene, a screen generation program used to generate various screens such as operation screens for specified functions, a history information recording program used to record log data such as operation logs and error logs, and the like.

The storage device 42 includes a setting information storage unit 42*b* configured to store various setting information on a plurality of devices for each scene, information on the most suitable reference material for each scene, and other information. Specifically, in the setting information storage unit 42*b*, set values for various devices used in each scene by surgical staff, information on the most suitable reference material for each scene displayed during scene selection, and other information have been set in advance.

More specifically, the setting information storage unit 42*b* stores information (hereinafter referred to as setting information) about one or more devices used in each scene as various setting information on a plurality of devices for each scene. Examples of set values include ON or OFF, output values, and thresholds of the device(s).

Furthermore, as information on the most suitable reference material for each scene, the setting information storage unit 42*b* stores at least one piece of information out of: the most suitable page number of an instruction manual for each scene, the most suitable chapter of a movie for each scene, and display timing.

When scene selection is made by the surgical staff, the control unit 41 reads setting information on each device relevant to the scene selected out of the setting information storage unit 42*b* and executes a collective setting program to make settings on a plurality of corresponding devices.

Furthermore, the storage device 42 includes a history information storage unit 42*c* serving as an operation log information storage unit configured to store, as log data, operation information (operation logs) about operations performed by the surgical staff with respect to one or more controlled devices.

The surgical staff performs a surgical operation by making scene selection and operating desired devices including the endoscopes 31 and 32 and the treatment instrument 13*a* such as an electrocautery connected to the electrocautery device 13. The treatment instrument 13*a* is turned on and off using a foot switch 13*b* connected to the electrocautery device 13. History information about operations performed by the surgical staff is stored as log data in the history information storage unit 42*c*.

The storage device 42 also includes an error information storage unit 42*d* configured to store, as log data, error information (error logs) about errors generated during collective settings or during operations of various devices.

The communications I/F 43, which is connected with a plurality of communications lines connected to a plurality of devices, is an interface circuit used by the control unit 41 to communicate with the plurality of devices. Of the plurality of devices, FIG. 2 shows the shadowless lights 3, the room light 7, the electrocautery device 13, the video processor 15, the light source device 16, and a server/cloud 51. Thus, the control unit 41 can communicate with the plurality of devices via the communications I/F 43 and thereby turn on and off each of the devices, establish or change set values, acquire log data such as operation information or error information from each of the devices, display information on the most suitable reference material, and so on.

Furthermore, the control unit 41 receives operation signals from the operating panels 21 and 21A and outputs image signals of display screens to the operating panels 21 and 21A via the display I/F 44 in order for the display screens to be displayed on the liquid crystal displays of the operating panels 21 and 21A.

On the display screen of the operating panel 21 or 21A, the surgical staff can instruct various devices to be operated and receive operation information, error information, and the like when the devices are operated on the display screen.

The operations performed by the surgical staff with respect to the operating panel 21 or 21A as well as errors occurring as a result of the operations are recorded as log data in the history information storage unit 42*c* and the error information storage unit 42*d*, respectively.

(Operation)

Next, a collective setting process of the system controller 22 in the above-mentioned surgery system 1 will be described.

Figure 3:
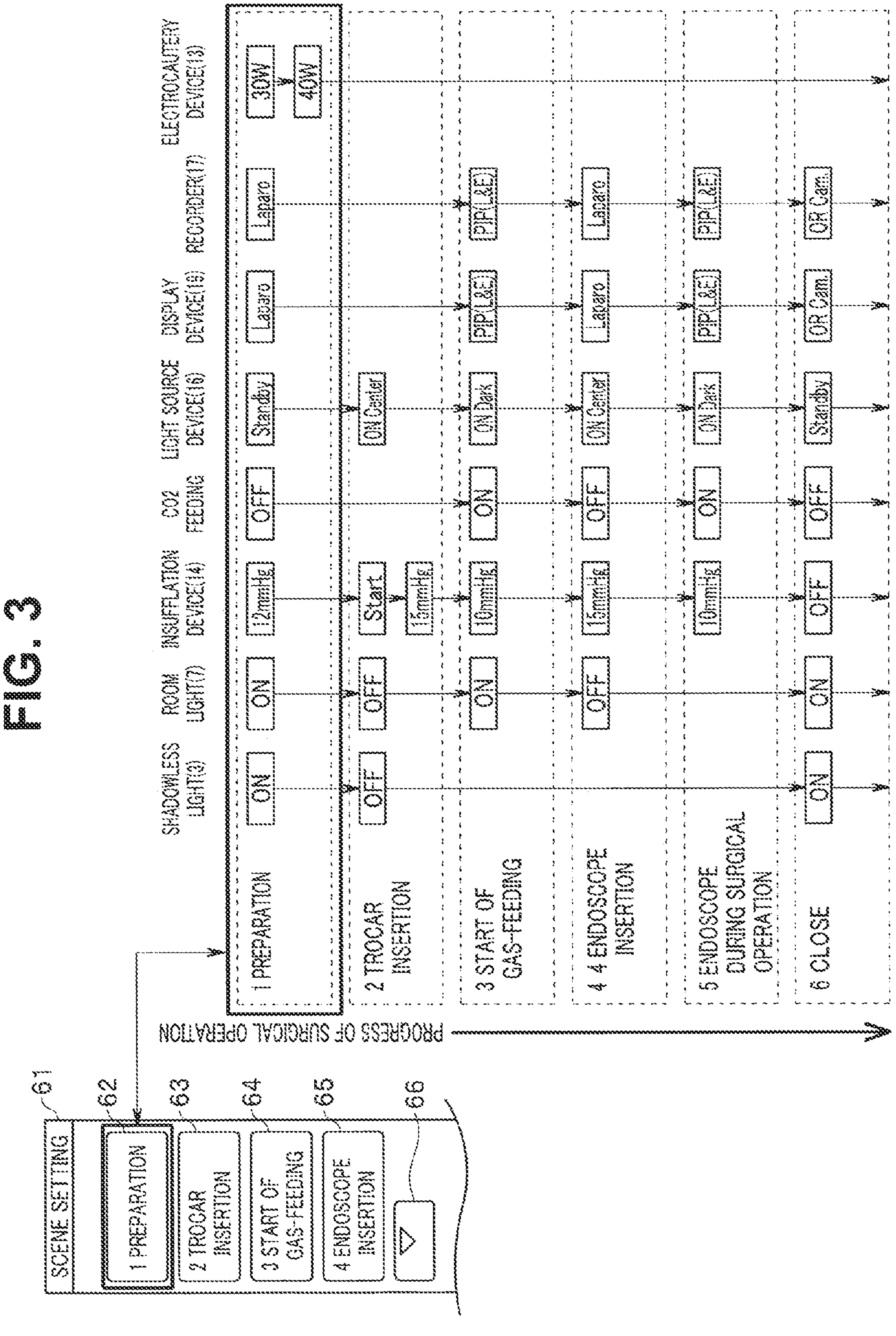
FIG. 3 is a diagram for explaining collective settings for a plurality of devices made by a scene selection function.

FIG. 3 is a diagram for explaining collective settings for a plurality of devices made by a scene selection function.

A scene setting screen 61 used to make scene settings, which is a scene selection function, is displayed on part of the operating panel 21. Note that the scene setting screen 61 may be displayed on another display device such as the operating panel 21A.

The scene setting screen 61 includes a plurality of scene selection buttons 62, 63, 64, and 65 for use by the surgical staff to select scenes in a surgical operation, and an operation button 66 that provides a scroll function or a page-turning function. By touching desired one of the scene selection buttons 62, 63, 64, and 65 according to the progress of the surgical operation, the surgical staff can collectively set states of a plurality of devices. In the example of FIG. 3, the plurality of devices are the shadowless lights 3, the room light 7, the insufflation device 14, the light source device 16, the display device 19, the recorder 17, and the electrocautery device 13.

By touching, for example, the scene selection button 62, a user can collectively set the states of a plurality of devices described above such as on/off states, running/stopped states of various functions, and output levels.

FIGS. 4A, 4B, 4C, and 4D are diagrams for explaining a setting screen used to make scene settings.

Figure 4A:
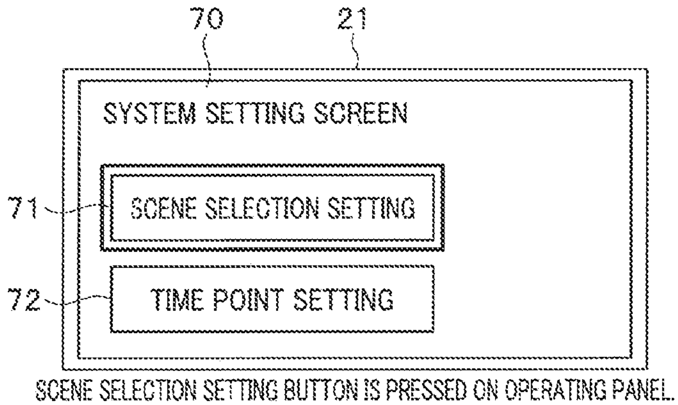
FIG. 4A is a diagram for explaining a setting screen used to make scene settings.
Figure 4B:
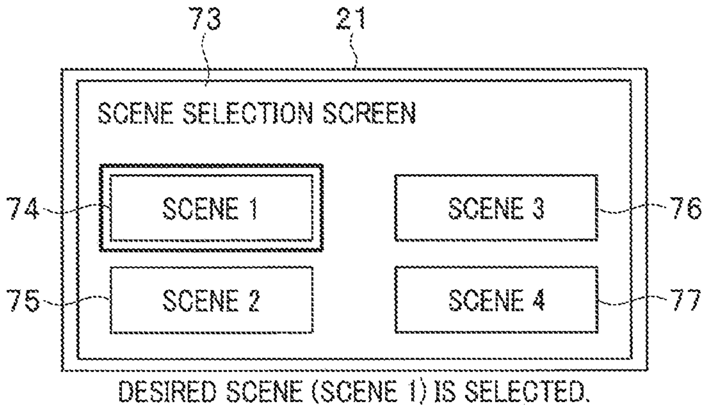
FIG. 4B is a diagram for explaining a setting screen used to make scene settings.

The user performs a desired operation on the operating panel 21 and causes the operating panel 21 to display a system setting screen 70 for use in system setting on the operating panel 21. As shown in FIG. 4A, the system setting screen 70 contains a scene selection setting button 71 for use to make scene settings and a time point setting button 72 for use to set time points. When the user touches (presses) the scene selection setting button 71 on the system setting screen 70, a scene selection screen 73 shown in FIG. 4B is displayed on the operating panel 21.

The scene selection screen 73 has a plurality of scene setting buttons 74 to 77 for use to set scenes. The scene setting button 74 is used to set a first scene, the scene setting button 75 is used to set a second scene, the scene setting button 76 is used to set a third scene, and the scene setting button 77 is used to set a fourth scene.

Figure 4C:
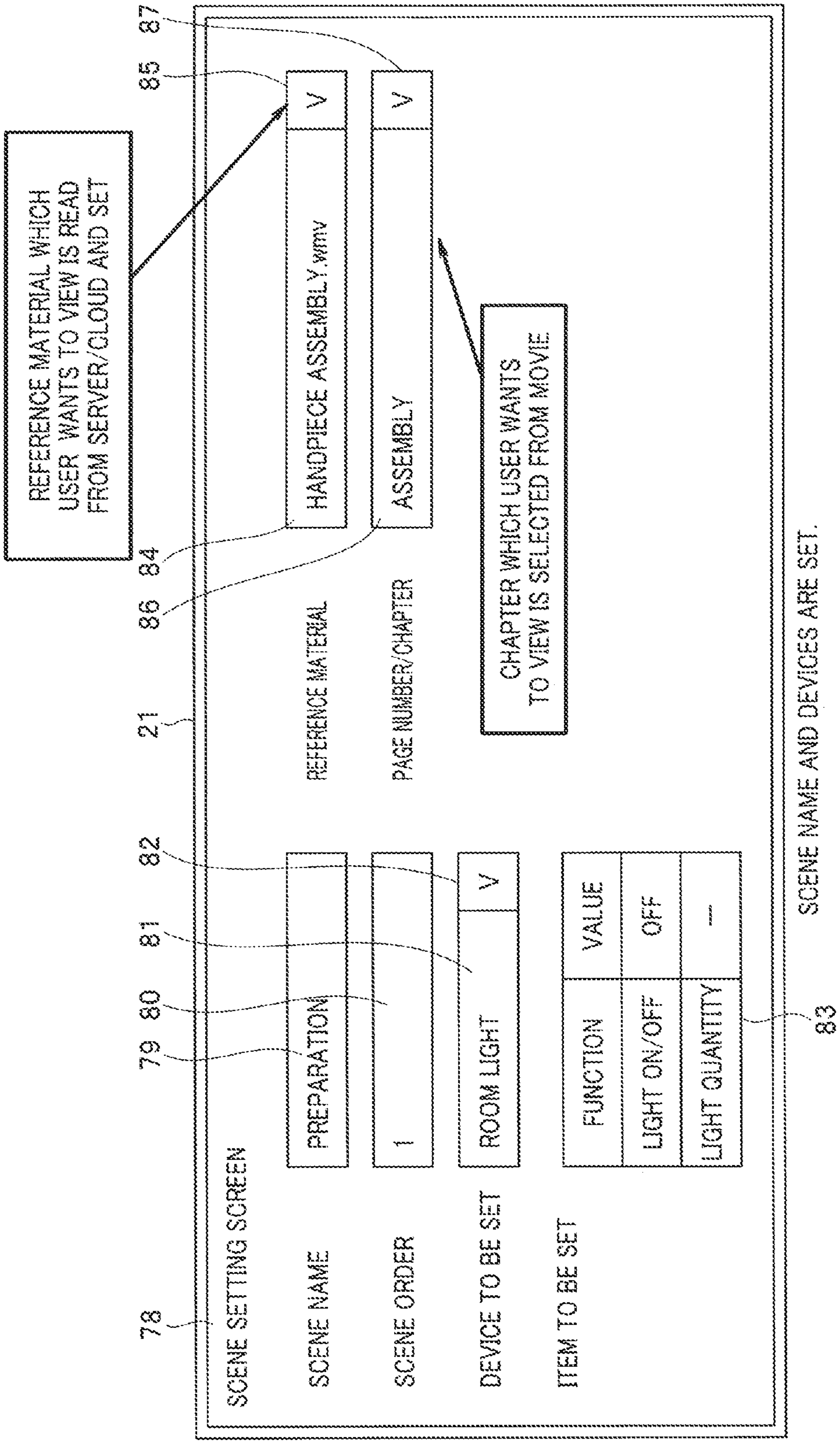
FIG. 4C is a diagram for explaining a setting screen used to make scene settings.

When the user wants to set, for example, the first scene, if the user touches the scene setting button 74 on the scene selection screen 73, a scene setting screen 78 shown in FIG. 4C is displayed on the operating panel 21.

Using the scene setting screen 78, the user sets a scene name and each device. The scene setting screen 78 contains a setting field 79 in which a scene name is indicated, a setting field 80 in which a scene order is indicated, a setting field 81 in which the device to be set is indicated, a selection button 82 used to change a device to be set, a setting field 83 used to specify an item to be set, a setting field 84 in which a reference material is indicated, a selection button 85 used to select a reference material, a setting field 86 in which a page number/chapter of a reference material is indicated, and a selection button 87 used to select a page number/chapter of the reference material.

The user enters a scene name in the setting field 79 of the scene setting screen 78 in FIG. 4C. "Preparation" has been inputted as the scene name. The scene order corresponds to the scene selected. In other words, if scene 1 is selected on the scene selection screen 73 in FIG. 4B, "1" is inputted in the setting field 80 in which the scene order is indicated, and if scene 2 is selected, "2" is inputted in the setting field 80.

The setting field 81 displays the device to be set. Here, Room Light is displayed as the device to be set. The user sets ON/OFF, light quantity, and the like of the room light using a setting field 83. By changing the device to be set using the selection button 82, the user can set each device in the "Preparation" scene.

On the scene setting screen 78 a reference material which the user wants to view (a document such as an instruction manual, or a movie) in the scene is read from the server/cloud 51 and set, and a page number/chapter which the user wants to view is selected from the reference material. Documents such as instruction manuals as well as movies are stored in the server/cloud 51. The control unit 41 communicates with the server/cloud 51 via the communications I/F 43, acquires an instruction manual, a movie, and the like stored in the server/cloud 51, and discriminates and set the most suitable page number of the instruction manual, the most suitable chapter of the movie, and the like for each scene.

On the scene setting screen 78 in FIG. 4C, the movie of "Handpiece Assembly.wmv" is set as the reference material which the user wants to view, and an "Assembly" chapter of the movie has been set. A reference material to be set and the page number/chapter of the reference material are inputted automatically based on conditions described later, but the user can manually set the reference material and the page number/chapter of the reference material using the selection buttons 85 and 87.

Figure 4D:
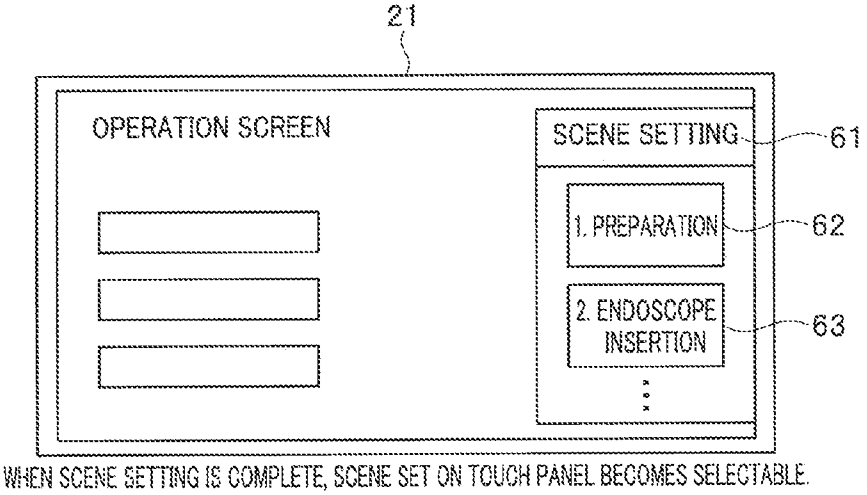
FIG. 4D is a diagram for explaining a setting screen used to make scene settings.

When all the scenes have been set on the scene setting screen 78 in FIG. 4C, the scene setting screen 61 is displayed on the operation screen shown in FIG. 4D. This makes it possible for the user to select desired scenes using the scene selection buttons 62, 63, etc. on the scene setting screen 61.

FIG. 5 is a diagram showing an example of scene setting details related to cholecystectomy procedures. In the cholecystectomy procedures, the first scene is set to "1. Preparation," the second scene is set to "2. Endoscope Insertion," the third scene is set to "3. Start of Handpiece Use," and the final scene is set to "End of Surgical Operation."

For example, in the scene of "1. Preparation," regarding device settings, the room light is set to OFF and the shadowless lights are set to OFF. As a reference material, the "Assembly" chapter of a movie of "Handpiece Assembly" has been set. Timing to display (play) the reference material is during scene selection, i.e., when the scene of "1. Preparation" is set. According to the present embodiment, the timing to display (play) the reference material is unified to "during scene selection."

In the scene of "2. Endoscope Insertion," page 70 of an instruction manual for a video system center is set as a reference material. The reference-material display timing is during scene selection as with "1. Preparation."

FIGS. 6A, 6B, 6C, and 6D are diagrams showing examples of a display screen for scene selection.

Figure 6A:
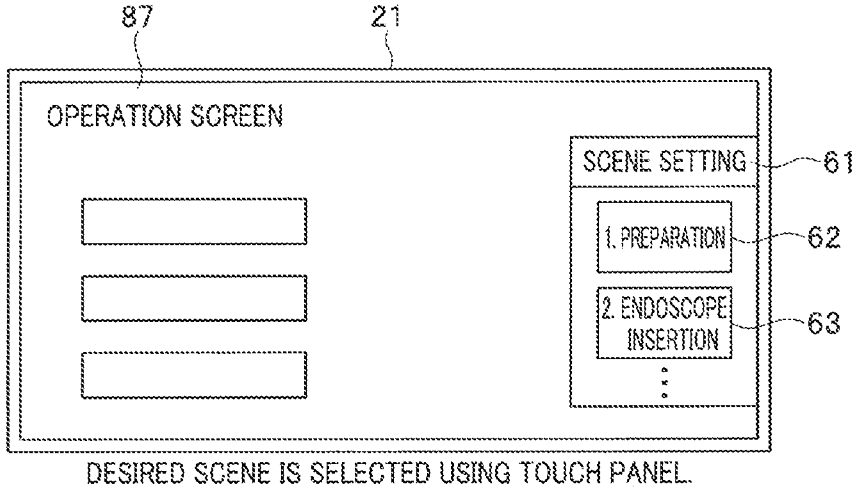
FIG. 6A is a diagram showing an example of a display screen for scene selection.
Figure 6B:
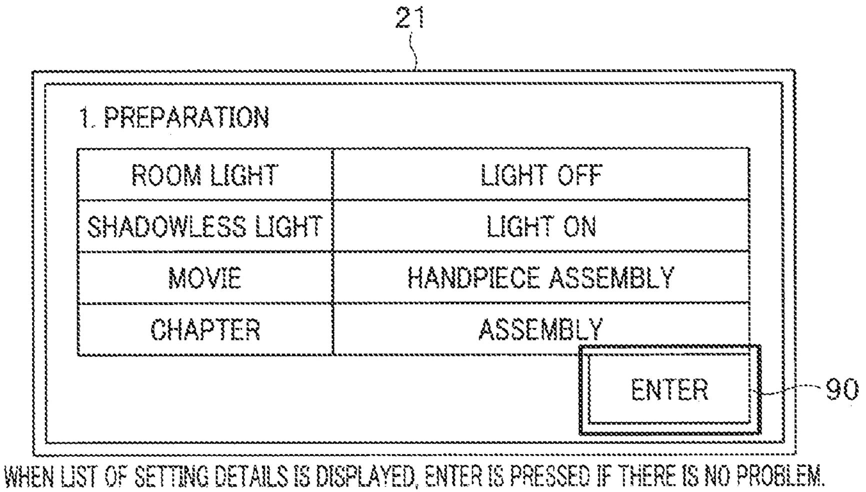
FIG. 6B is a diagram showing an example of a display screen for scene selection.
Figure 6C:
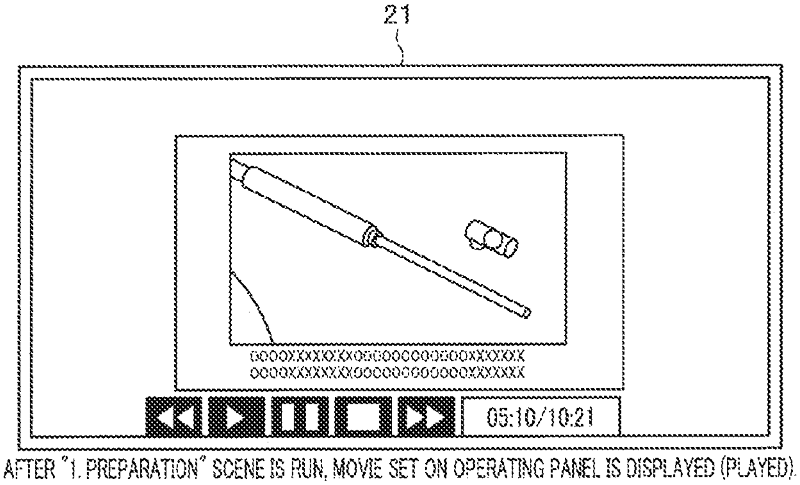
FIG. 6C is a diagram showing an example of a display screen for scene selection.

When the user touches the scene selection button 62 of "1. Preparation" on the scene setting screen 61 shown in FIG. 6A, a list of "1. Preparation" scene setting details is displayed as shown in FIG. 6B. If there is no problem with the setting details, the user touches an Enter button 90. Consequently, after the scene is run, i.e., after all the devices are set collectively, the movie chapter set on the operating panel 21 is displayed (played) as shown in FIG. 6C.

Figure 6D:
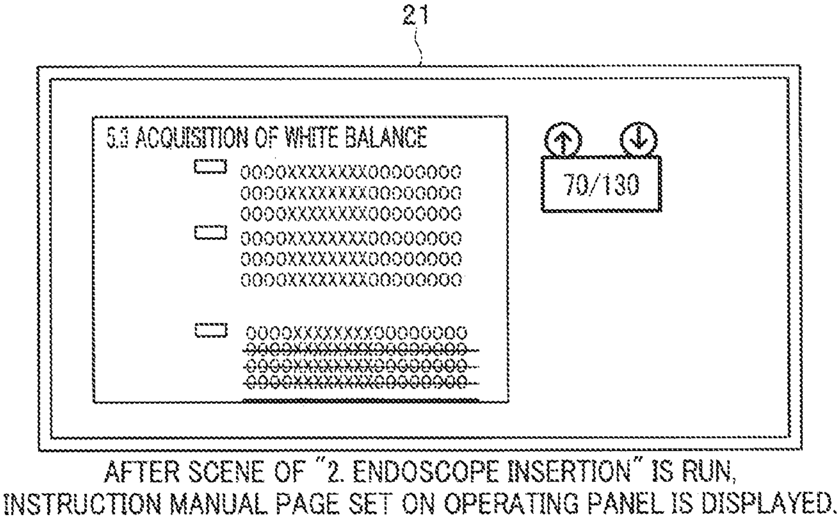
FIG. 6D is a diagram showing an example of a display screen for scene selection.

When the user touches the scene selection button 63 of "2. Endoscope Insertion" on the scene setting screen 61, after the scene is run, the set reference material page is displayed on the operating panel 21 as shown in FIG. 6D. Since page 70 of the instruction manual has been set for the scene of "2. Endoscope Insertion" as described above, page 70 of the instruction manual is displayed on the operating panel 21 as set above.

FIG. 7 is a diagram for explaining an example of search conditions for an instruction manual or a movie which a user wants to view.

The settings of the page number of an instruction manual and the chapter of a movie are determined based on the scene order and setting details shown in two sets of search conditions: search conditions A and search conditions B. Note that the concrete contents of the search conditions A and B are exemplary, and are not limited to the contents of FIG. 7. In other words, the control unit 41 can set the page number of an instruction manual or the chapter of a movie using conditions other than the search conditions A and B shown in FIG. 7. The search conditions A are "a. a scene order" and/or "b. a scene containing a specific device setting." The search conditions B are "a. to make the system controller store the page number of a reference material/the chapter of a movie manually referred to by the user in a certain scene in the past and reflect contents of the stored information," "b. to discriminate a device used in each scene based on a procedure, a device to be used, and setting details, discriminate a reference material/movie based on the device name, and set the page number of a reference material/the chapter of a movie set according to the name/order of the scene," "c. to take a picture of a device using a camera or the like/read a barcode, an RFID, or the like, discriminate the reference material/movie of the device and set the page number of a reference material/the chapter of a movie set according to the name/order of the scene," and "d. to discriminate the reference material/movie of the device based on equipment and materials to be used and set the page number of a reference material/the chapter of a movie set according to the name/order of the scene."

For example, the control unit 41 sets information which the user wants to view based on "a. the scene to be run first" of the search conditions A as well as on "a. to search for a movie and chapter of a handpiece assembly method referred to in the past in the scene to be run first and set search results for scene." Consequently, the chapter name "assembly" of the handpiece assembly movie is set.

Based on the search conditions A and B, in the second scene, the page of "Instruction Manual for Video System Center" to be displayed is set to "page 70," in the third scene, the chapter name of the movie of "How to Use Handpiece" is set to "How to Use," and in the fourth scene, page of "Cleanup Method for Devices, Instruction Manual for Storage Space" to be displayed is set to "page 120."

Figure 8:
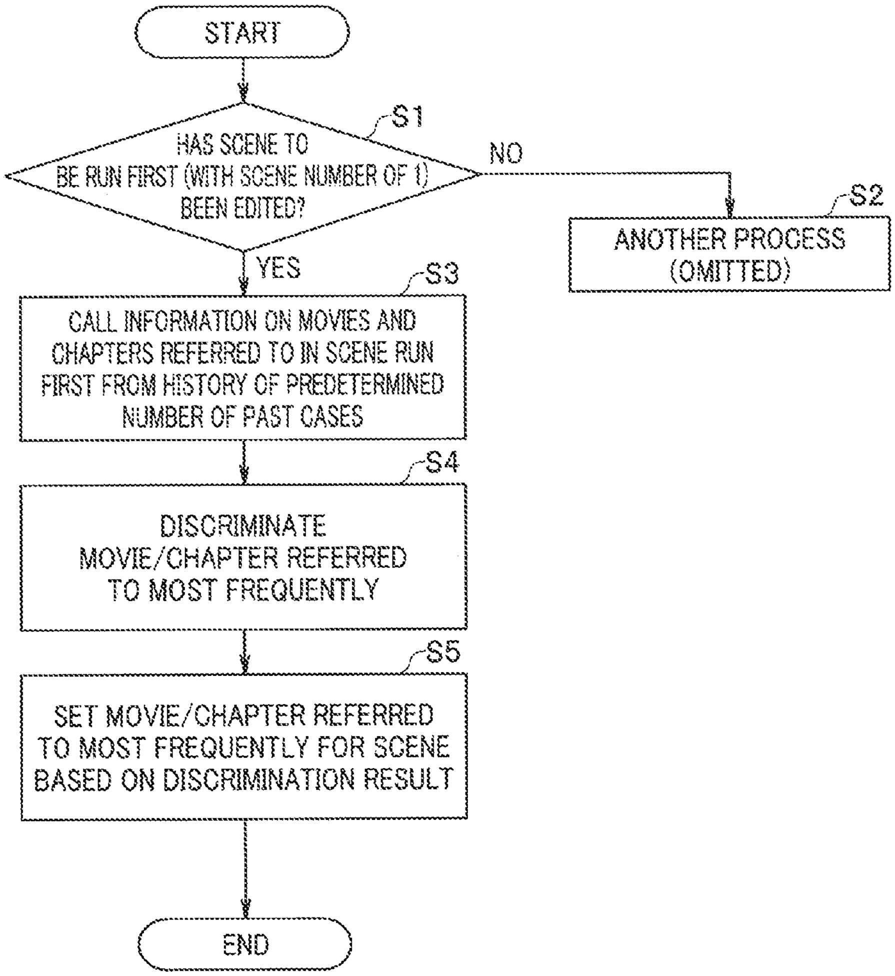
FIG. 8 is a flowchart showing a process flow of reference material setting in a "1. Preparation" scene.

FIG. 8 is a flowchart showing a process flow of reference material setting in a "1. Preparation" scene.

The control unit 41 determines whether the scene to be run first (with a scene number of 1) has been edited (51). If it is determined that the scene to be run first (with a scene number of 1) has not been edited, the control unit 41 performs another process (S2). After performing the other process, the control unit 41 may either return to the first process of the flowchart or finish processing the flowchart.

On the other hand, if it is determined that the scene to be run first (with a scene number of 1) has been edited, the control unit 41 calls information on the movies and chapters referred to in the scene run first from a history of a predetermined number of past cases (S3).

Next, the control unit 41 discriminates the movie/chapter referred to most frequently from the called history (S4). Based on the discrimination result, the control unit 41 sets the movie/chapter referred to most frequently for the scene (S5) and finishes processing.

Figure 9:
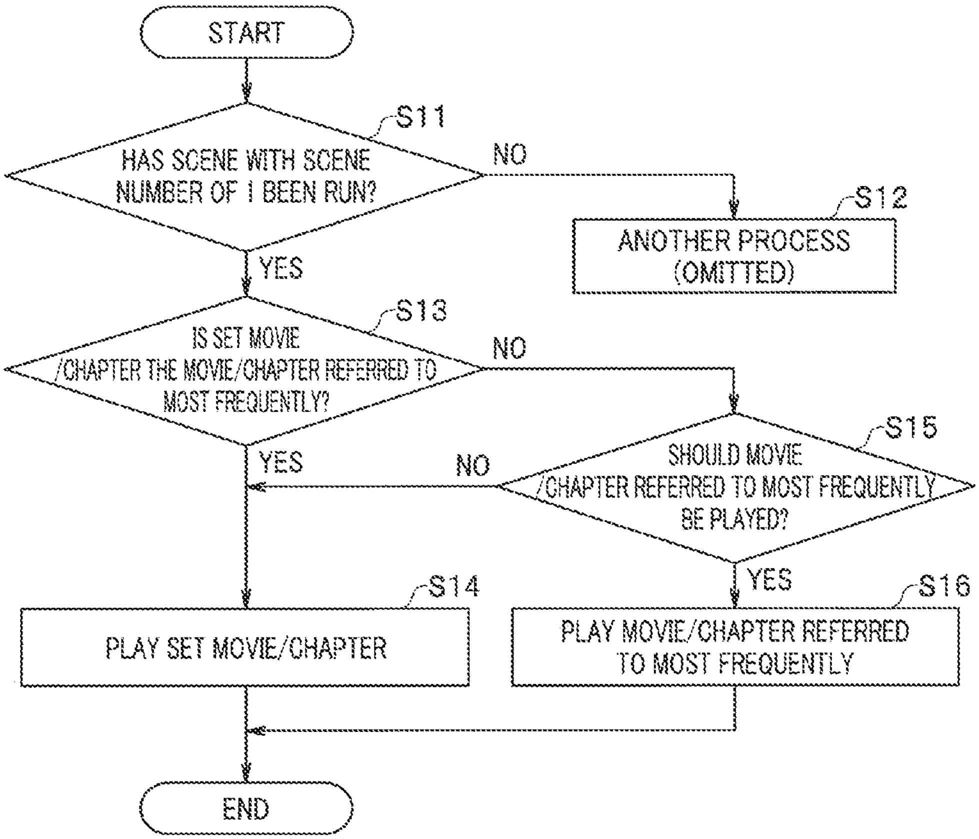
FIG. 9 is a flowchart showing a process flow of scene selection in the "1. Preparation" scene.

FIG. 9 is a flowchart showing a process flow of scene selection in the "1. Preparation" scene.

The control unit 41 determines whether the scene with a scene number of 1 has been run (S11). If it is determined that the scene with a scene number of 1 has not been run, the control unit 41 performs another process (S12). After performing the other process, the control unit 41 may either return to the first process of the flowchart or finish processing the flowchart.

On the other hand, if it is determined that the scene with a scene number of 1 has been run, the control unit 41 determines whether the set movie/chapter is the movie/chapter referred to most frequently (S13). In other words, the control unit 41 discriminates the movie/chapter referred to most frequently in the process of FIG. 8 and sets the movie/chapter for the scene, but the movie/chapter referred to most frequently may have changed when a scene selection is made actually. Therefore, the control unit 41 determines whether the set movie/chapter is the one referred to most frequently.

If it is determined that the set movie/chapter is the one referred to most frequently, the control unit 41 plays the set movie/chapter (S14) and finishes processing. On the other hand, if it is determined that the set movie/chapter is not the one referred to most frequently, the control unit 41 determines whether to play the movie/chapter referred to most frequently (S15).

If it is determined not to play the movie/chapter referred to most frequently, the control unit 41 goes to the process of S14, plays the set movie/chapter (S14), and finishes processing. On the other hand, if it is determined to play the movie/chapter referred to most frequently, the control unit 41 plays the movie/chapter referred to most frequently (S16) and finishes processing.

Figure 10:
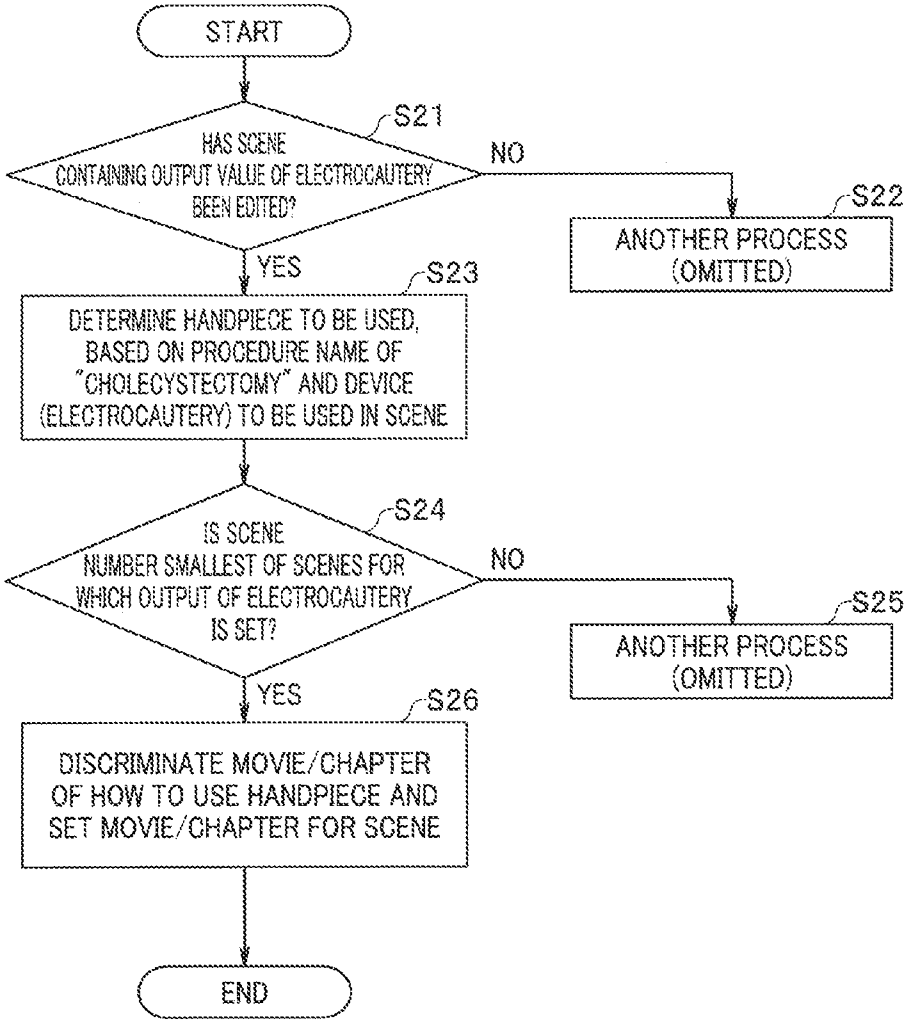
FIG. 10 is a flowchart showing a process flow of reference material setting in a "3. Start of handpiece use" scene.

FIG. 10 is a flowchart showing a process flow of reference material setting in a "3. Start of handpiece use" scene.

The control unit 41 determines whether a scene containing an output value of an electrocautery has been edited (S21). If it is determined that a scene containing an output value of an electrocautery has not been edited, the control unit 41 performs another process (S22). After performing the other process, the control unit 41 may either return to the first process of the flowchart or finish processing the flowchart.

On the other hand, if it is determined that a scene containing an output value of an electrocautery has been edited, the control unit 41 discriminates a handpiece to be used, based on the procedure name of "cholecystectomy" and the device (electrocautery) to be used in the scene (S23).

The control unit 41 determines whether the scene number is the smallest of the scenes for which output of an electrocautery is set (S24). If it is determined that the scene number is not the smallest of the scenes for which output of an electrocautery is set, the control unit 41 performs another process (S25). After performing the other process, the control unit 41 may either return to the first process of the flowchart or finish processing the flowchart.

On the other hand, if it is determined that the scene number is the smallest of the scenes for which output of an electrocautery is set, the control unit 41 discriminates the movie/chapter of how to use a handpiece, sets the movie/chapter for the scene (S26), and finishes processing.

Figure 11:
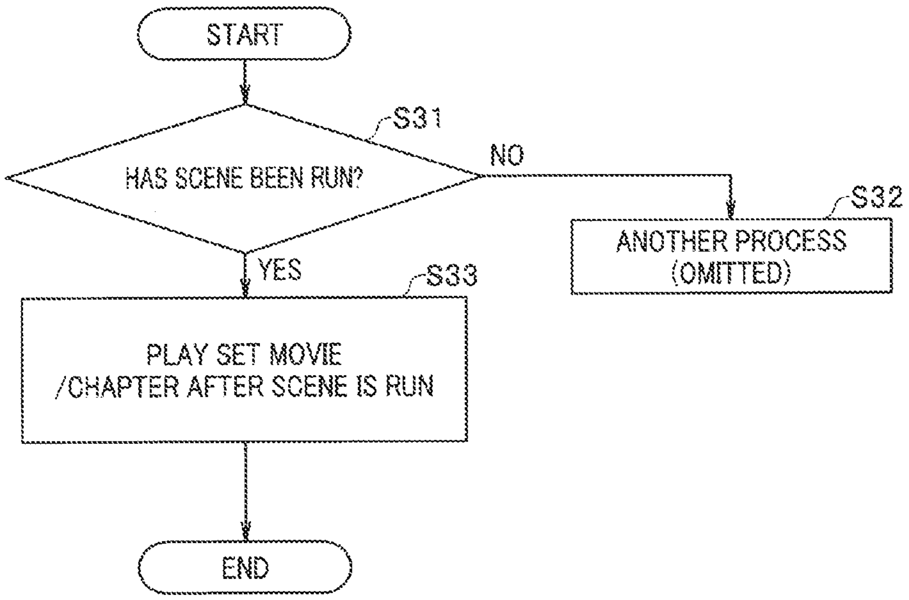
FIG. 11 is a flowchart showing a process flow of scene selection in the "3. Start of handpiece use" scene.

FIG. 11 is a flowchart showing a process flow of scene selection in the "3. Start of handpiece use" scene.

The control unit 41 determines whether the scene has been run (S31). In the process of S31, the control unit 41 determines whether the "3. Start of handpiece use" scene has been run. If it is determined that the scene has not been run, the control unit 41 performs another process (S32). After performing the other process, the control unit 41 may either return to the first process of the flowchart or finish processing the flowchart.

On the other hand, if it is determined that the scene has been run, the control unit 41 plays the set movie/chapter after the scene is run (S33) and finishes processing. As a result, the control unit 41 plays the set "How to Use" chapter of the "How to Use Handpiece" movie in the "3. Start of handpiece use" scene.

As described above, the control unit 41 of the system controller 22 discriminates and sets a reference material—here, the page number of an instruction manual or the chapter of a movie—most suitable for the scene during scene setting based on the scene order and setting details. When the set scene is run, the control unit 41 sets all the devices collectively and displays a relevant page of the instruction manual or plays a relevant chapter of the movie.

In other words, after the scene selection is made, the control unit 41 displays the reference material and plays the movie with the set timing, and thus can display only necessary information with appropriate timing according to each scene, allowing the user to efficiently proceed with tasks.

Thus, the central control apparatus according to the present embodiment allows information about tasks carried out according to the progress of a surgical operation to be displayed timely according to the progress of the surgical operation. As a result, the control unit 41 can aid tasks occurring in the progress of the surgical operation, increasing efficiency of the surgical operation performed by the user. Note that search conditions for the information about the tasks carried out according to the progress of the surgical operation are not limited to the search conditions A and search conditions B in FIG. 7, and other search conditions are also applicable.

Second Embodiment

Next, a second embodiment will be described.

In the first embodiment, the timing to play the page number of an instruction manual or the chapter of a movie is limited to when a scene selection is made. In contrast, the second embodiment allows the timing to display the page number of an instruction manual or play the chapter of a movie to be specified.

Figure 12:
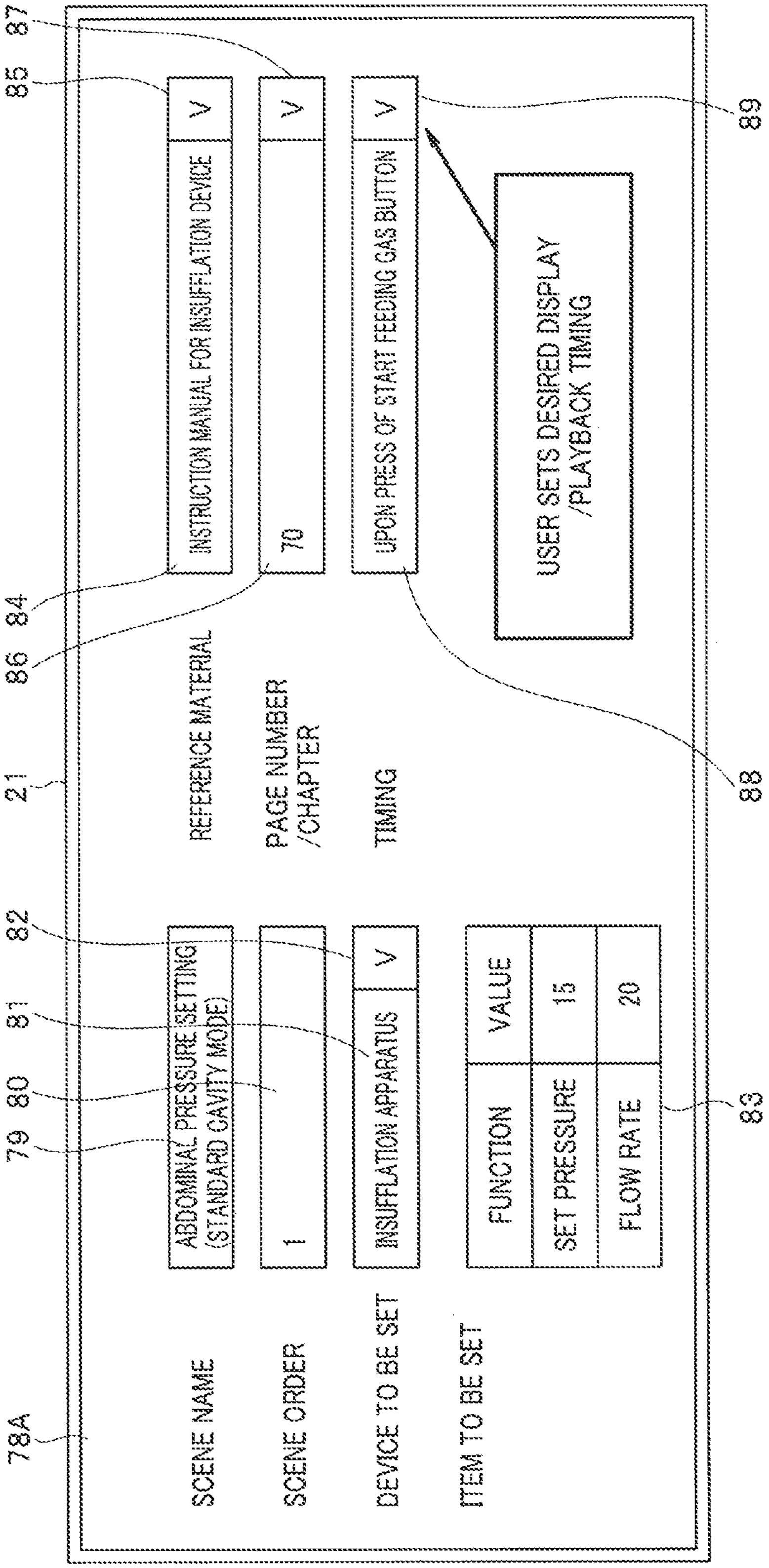
FIG. 12 is a diagram for explaining a setting screen used to make scene settings.

FIG. 12 is a diagram for explaining a setting screen used to make scene settings. Note that in FIG. 12, components similar to those in FIG. 4C are denoted by the same reference numerals as the corresponding components, and description thereof will be omitted.

As shown in FIG. 12, in addition to the components of the scene setting screen 78 in FIG. 4C, a scene setting screen 78A includes a setting field 88 and a selection button 89 that are used to set the timing to display the page number/chapter of a reference material (instruction manual or movie).

By touching the scene selection button 89, the user can set the timing to display/play the reference material (instruction manual or movie). In the example of FIG. 12, as a display/playback timing, "upon press of Start Feeding Gas button" is provided in the setting field 88, and when the user presses the Start Feeding Gas button of the insufflation device 14, page 70 of the instruction manual for the insufflation device is displayed.

FIG. 13 is a diagram showing an example of registration contents set for each procedure and scene. As shown in FIG. 13, in an abdominal pressure setting (standard cavity mode) scene in a general cholecystectomy procedure, the set pressure of the insufflation device is set to 15 mmHg as device setting, page 70 of the instruction manual for the insufflation device is set as a reference material, and "upon press of Start Feeding Gas button" of the insufflation device is set as reference-material display timing.

On the other hand, in an abdominal pressure setting (small cavity mode) scene in a pediatric cholecystectomy procedure, the set pressure of the insufflation device is set to 12 mmHg as device setting, page 75 of the instruction manual for the insufflation device is set as a reference material, and "upon press of Start Feeding Gas button" of the insufflation device is set as reference-material display timing.

Figure 14:
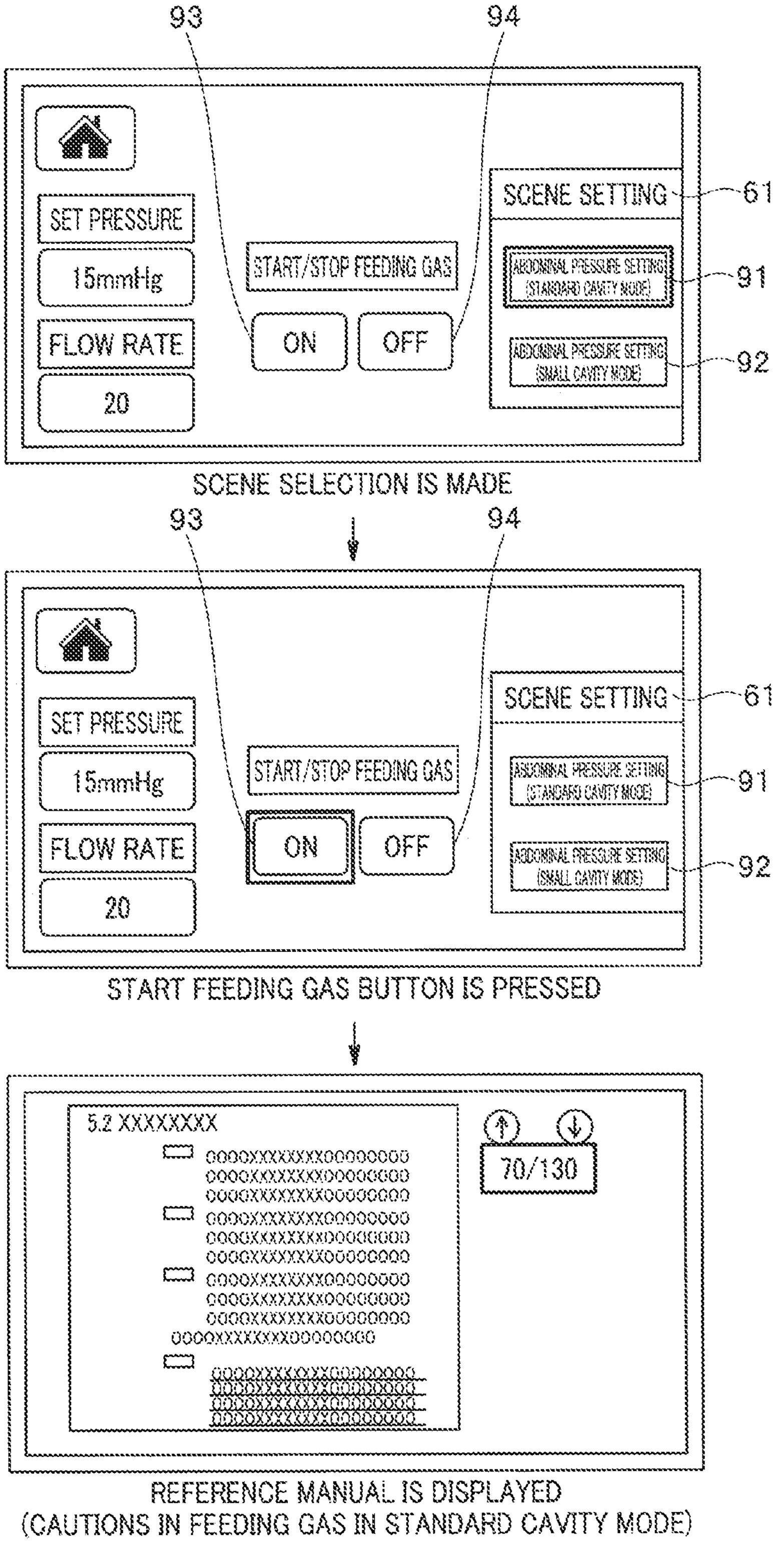
FIG. 14 is a diagram showing an example of screen display appearing when an abdominal pressure setting (standard cavity mode) scene is selected.
Figure 15:
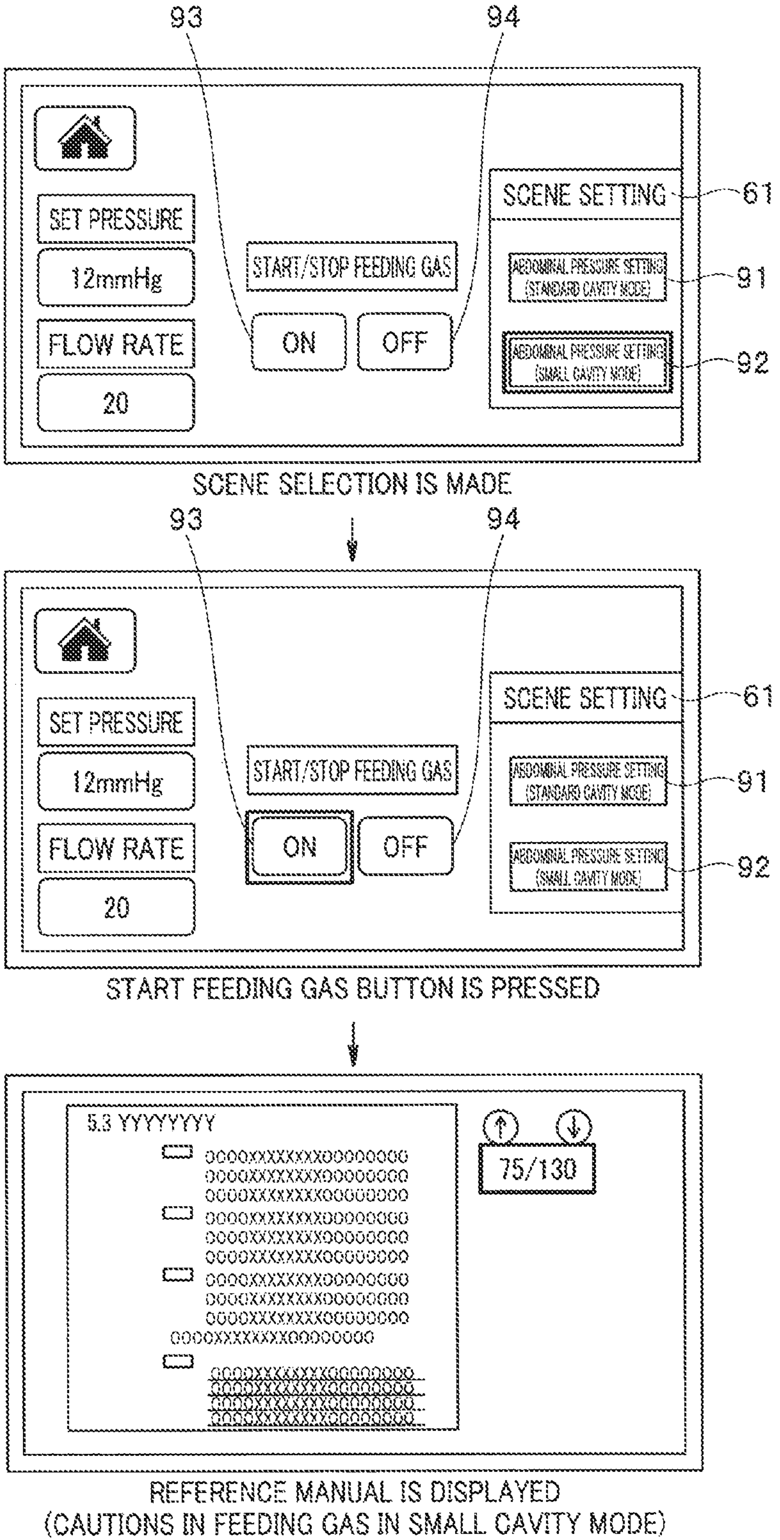
FIG. 15 is a diagram showing an example of screen display appearing when an abdominal pressure setting (small cavity mode) scene is selected.

FIG. 14 is a diagram showing an example of screen display appearing when an abdominal pressure setting (standard cavity mode) scene is selected and FIG. 15 is a diagram showing an example of screen display appearing when an abdominal pressure setting (small cavity mode) scene is selected.

As shown in FIG. 14, the scene setting screen 61 includes a scene selection button 91 for use to select an abdominal pressure setting (standard cavity mode) scene and a scene selection button 92 for use to select an abdominal pressure setting (small cavity mode) scene. When the user presses the scene selection button 91 for use to select an abdominal pressure setting (standard cavity mode) scene, a device setting is made. Here, the set pressure of the insufflation device is set to 15 mmHg. Furthermore, the device setting screen includes a Start Feeding Gas button 93 for use to start feeding gas and a Stop Feeding Gas button 94 for use to stop feeding gas.

When the user presses the Start Feeding Gas button 93, according to the set reference-material display timing, the control unit 41 displays page 70 of the instruction manual that contains cautions in feeding gas in standard cavity mode.

On the other hand, as shown in FIG. 15, when the user presses the scene selection button 92 for use to select an abdominal pressure setting (small cavity mode) scene, a device setting is made. Here, the set pressure of the insufflation device is set to 12 mmHg. Then, when the user presses the Start Feeding Gas button 93, according to the set reference-material display timing, the control unit 41 displays page 75 of the instruction manual that contains cautions in feeding gas in small cavity mode.

FIG. 16 is a diagram showing search conditions for a reference material to be set.

In the general cholecystectomy procedure, the set pressure of the insufflation device has been set to 15 mmHg, and the standard cavity mode is discriminated based on the procedure name and the set pressure. Consequently, the page that has a page number of 70 and contains cautions in feeding gas in standard cavity mode is set for the scene.

On the other hand, in the pediatric cholecystectomy procedure, the set pressure of the insufflation device is set to 12 mmHg, and the small cavity mode is discriminated based on the procedure name and the set pressure. Consequently, the page that has a page number of 75 and contains cautions in feeding gas in small cavity mode is set for the scene.

Figure 17:
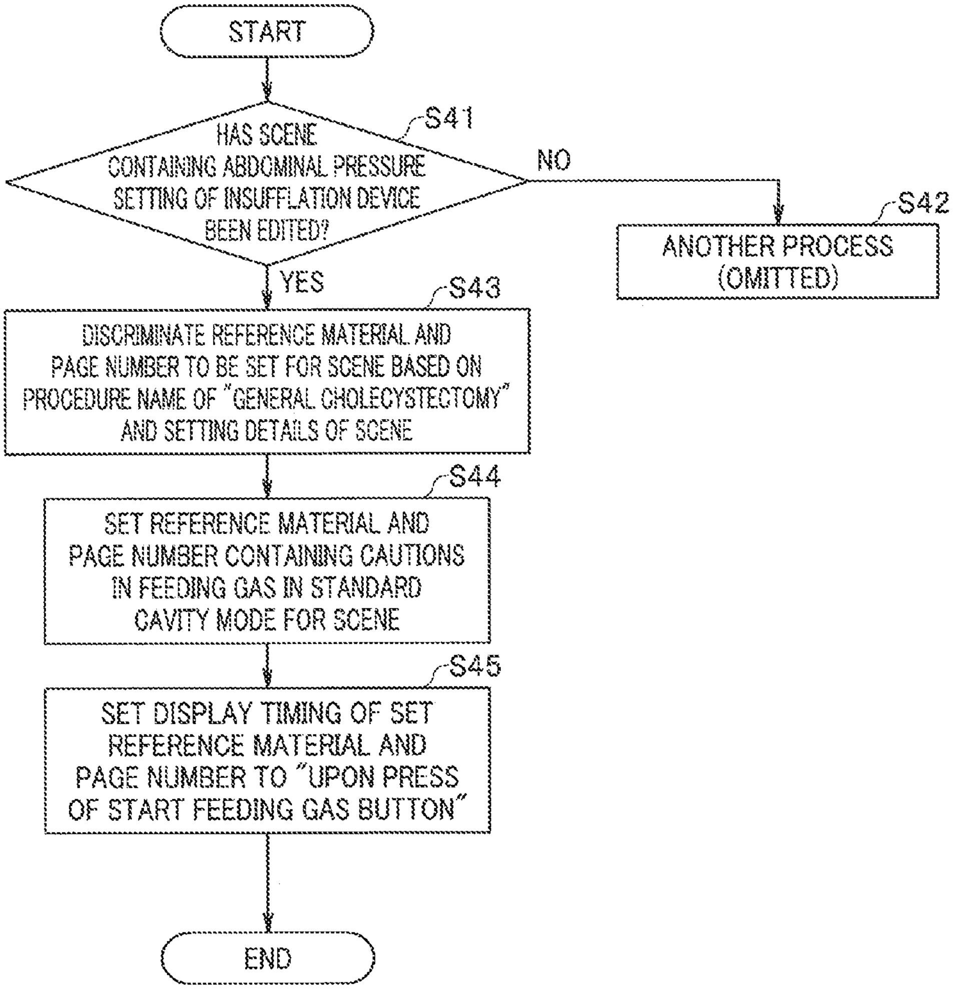
FIG. 17 is a flowchart showing a process flow of reference material setting in abdominal pressure setting (standard cavity mode) scene.

FIG. 17 is a flowchart showing a process flow of reference material setting in abdominal pressure setting (standard cavity mode) scene.

The control unit 41 determines whether a scene containing an abdominal pressure setting of the insufflation device has been edited (S41). If it is determined that a scene containing an abdominal pressure setting of the insufflation device has not been edited, the control unit 41 performs another process (S42). After performing the other process, the control unit 41 may either return to the first process of the flowchart or finish processing the flowchart.

On the other hand, if it is determined that a scene containing an abdominal pressure setting of the insufflation device has been edited, the control unit 41 discriminates the reference material and page number to be set for the scene, based on the procedure name "general cholecystectomy" and the scene setting details (S43). Based, for example, on the set pressure of the insufflation device, the control unit 41 discriminates the instruction manual for the insufflation device and the page number of the page containing cautions in feeding gas in standard cavity mode.

Once the reference material and page number containing cautions in feeding gas in standard cavity mode are discriminated in the process of S43, the control unit 41 sets the instruction manual and page number for the scene (S44). Finally, the control unit 41 sets the timing to display the set reference material and page number to "upon press of Start Feeding Gas button" (S45) and finishes processing.

Figure 18:
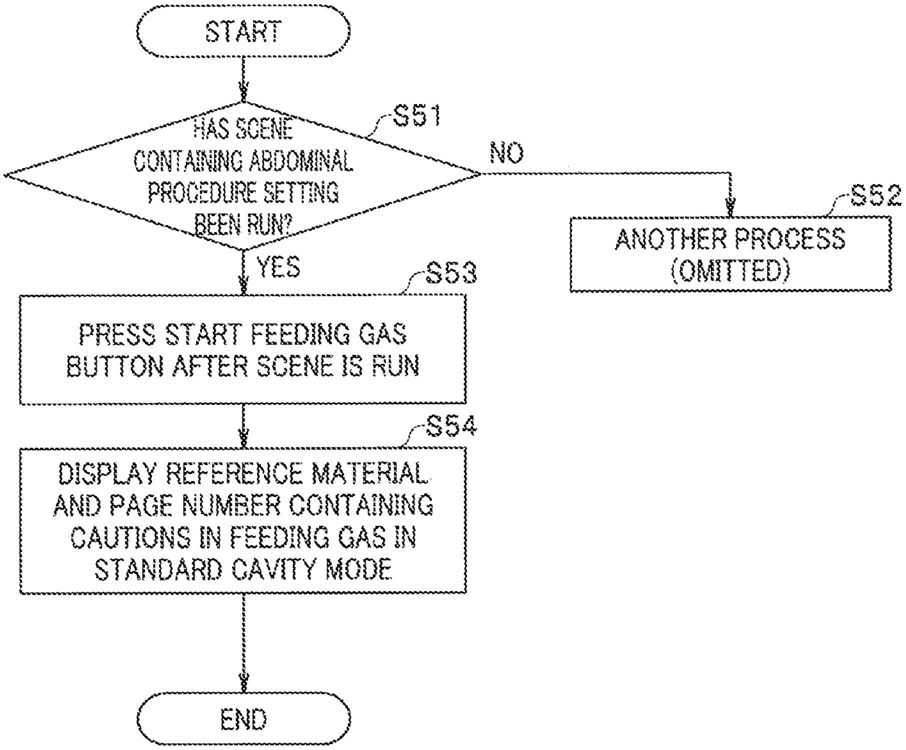
FIG. 18 is a flowchart showing a process flow of scene selection in an abdominal pressure setting (standard cavity mode) scene.

FIG. 18 is a flowchart showing a process flow of scene selection in an abdominal pressure setting (standard cavity mode) scene.

The control unit 41 determines whether a scene containing an abdominal pressure setting has been run (SM). If it is determined that a scene containing an abdominal pressure setting has not been run, the control unit 41 performs another process (S52). After performing the other process, the control unit 41 may either return to the first process of the flowchart or finish processing the flowchart.

On the other hand, if it is determined that a scene containing an abdominal pressure setting has been run, when the Start Feeding Gas button is pressed after the scene is run (S53), the control unit 41 displays the reference material and page number containing cautions in feeding gas in standard cavity mode (S54) and finishes processing.

As described above, by setting, during scene selection, the page number of an instruction manual or timing to play a movie, the control unit 41 of the system controller 22 allows the user to check necessary information with a desired timing and check precautions according to the progress of a surgical operation.

As the page number of an instruction manual or timing to play a movie is set during scene selection, the user can check necessary information with a desired timing and check precautions and deal with trouble quickly according to the progress of a surgical operation.

Third Embodiment

Next, a third embodiment will be described.

If a device error occurs during a procedure, by displaying a reference material or movie describing how to deal with the error, the third embodiment makes it possible to solve the error quickly.

Figure 19:
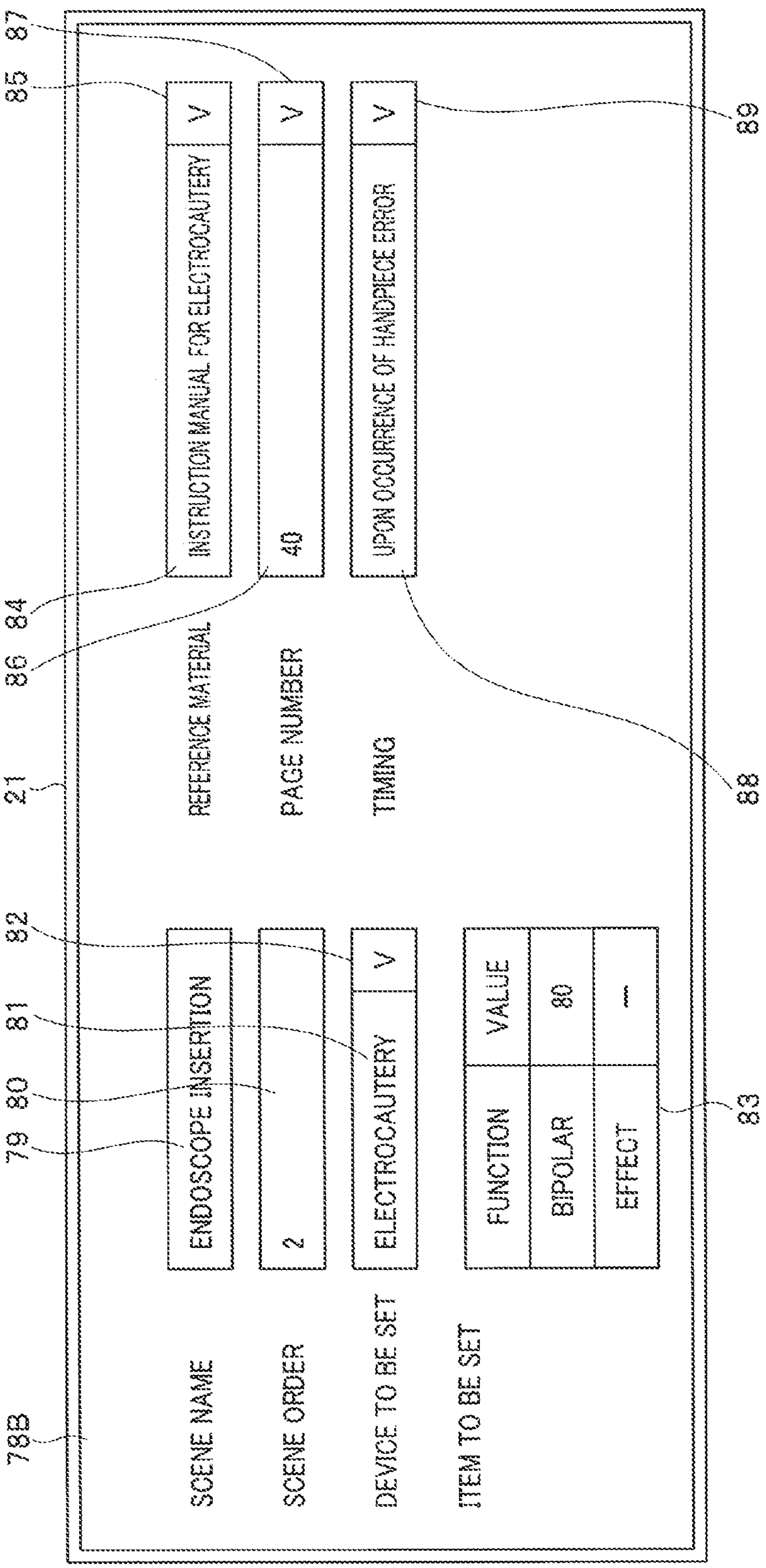
FIG. 19 is a diagram for explaining a setting screen used to make scene settings.

FIG. 19 is a diagram for explaining a setting screen used to make scene settings. Note that a scene setting screen 78B of FIG. 19 is identical in screen layout with the scene setting screen 78A of FIG. 12.

In the scene setting screen 78B of FIG. 19, page 40 of an instruction manual for an electrocautery is set as a reference material and "upon occurrence of handpiece error" is set as timing.

FIG. 20 is a diagram showing an example of registration contents set for each procedure and scene.

Regarding the registration contents set for each procedure and scene, when the procedure is cholecystectomy and the scene is endoscope insertion, according to the output value (80 W) of the electrocautery, the page to be displayed is set to page 40 of an electrocautery instruction manual describing how to deal with cholecystic handpiece output error, and display timing is set to "upon occurrence of electrocautery handpiece error."

On the other hand, regarding the registration contents set for each procedure and scene, when the procedure is gastrectomy and the scene is endoscope insertion, according to the output value (60 W) of the electrocautery, the page to be displayed is set to page 45 of an electrocautery instruction manual describing how to deal with gastric handpiece output error and display timing is set to "upon occurrence of electrocautery handpiece error."

Figure 22:
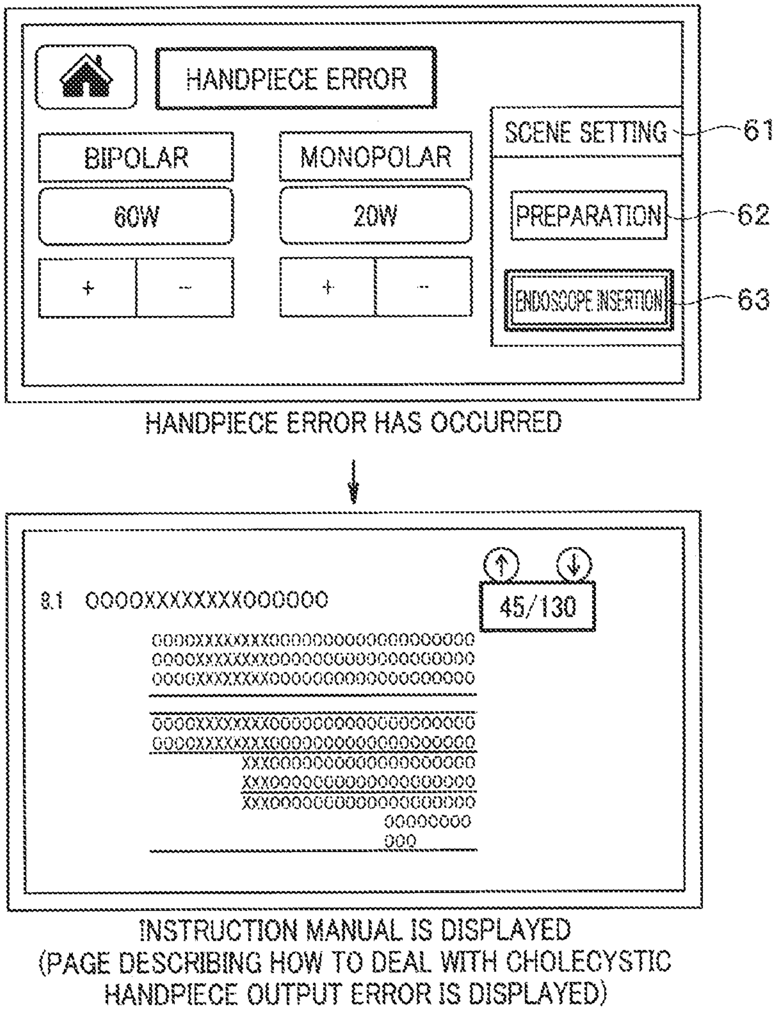
FIG. 22 is a diagram for explaining an example of a display screen appearing when a handpiece error occurs.

FIGS. 21 and 22 are diagrams for explaining examples of a display screen appearing when a handpiece error occurs.

As shown in FIG. 21, when the procedure is cholecystectomy, if a handpiece error occurs in an endoscope insertion scene, according to registration contents, the control unit 41 displays page 40 of the electrocautery instruction manual, i.e., the page that describes how to deal with cholecystic handpiece output error, on the operating panel 21.

On the other hand, as shown in FIG. 22, when the procedure is gastrectomy, if a handpiece error occurs in an endoscope insertion scene, according to registration contents, the control unit 41 displays page 45 of the electrocautery instruction manual, i.e., the page that describes how to deal with gastric handpiece output error, on the operating panel 21.

FIG. 23 is a diagram showing search conditions for a reference material to be set. As shown in FIG. 23, based on the scene in which device settings include an electrocautery output value as well as on the procedure (cholecystectomy) and the device to be used, the control unit 41 discriminates a reference material for a cholecystic handpiece. Also, the control unit 41 sets a page number describing how to deal with cholecystic handpiece output error for the scene, based on setting details (in case of handpiece output error).

On the other hand, based on the scene in which device settings include an electrocautery output value as well as on the procedure (gastrectomy) and the device to be used, the control unit 41 discriminates a reference material for a gastric handpiece. Also, the control unit 41 sets a page number describing how to deal with gastric handpiece output error for the scene, based on setting details (in case of handpiece output error).

Figure 24:
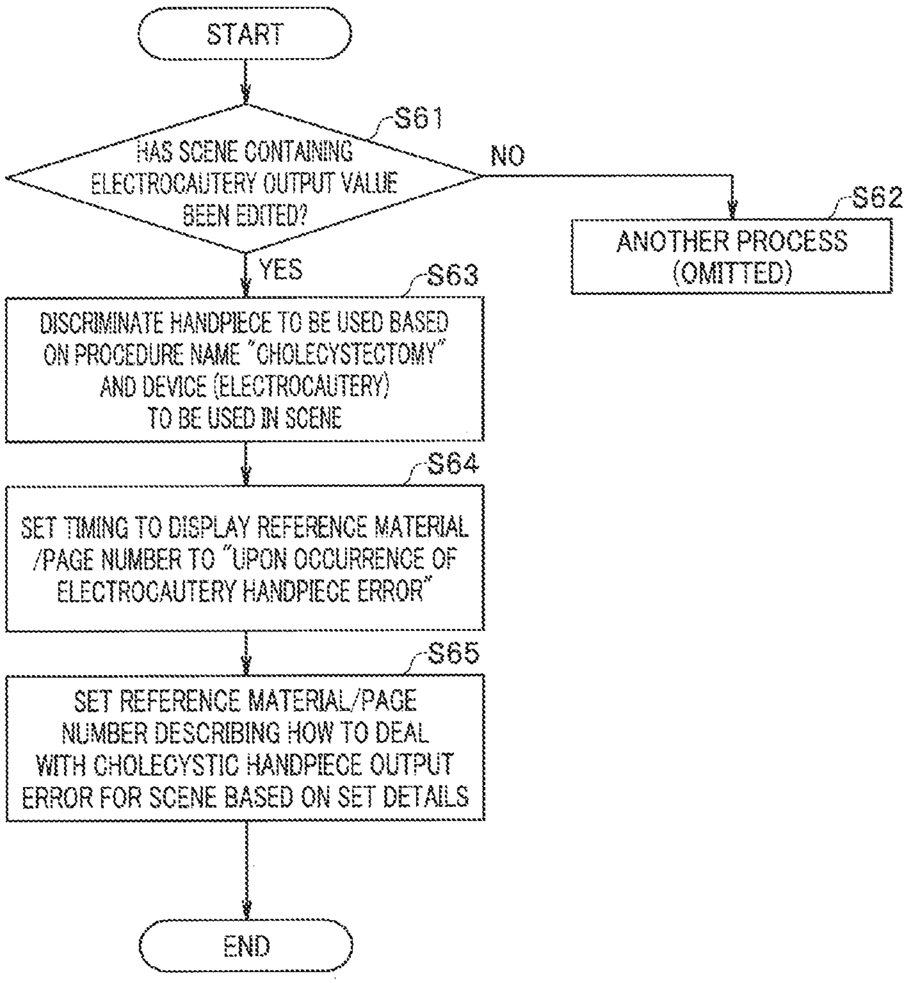
FIG. 24 is a flowchart showing a process flow of reference material setting in an endoscope insertion scene of cholecystectomy procedures.

FIG. 24 is a flowchart showing a process flow of reference material setting in an endoscope insertion scene of cholecystectomy procedures.

The control unit 41 determines whether a scene containing an electrocautery output value has been edited (S61). If it is determined that a scene containing an electrocautery output value has not been edited, the control unit 41 performs another process (S62). After performing the other process, the control unit 41 may either return to the first process of the flowchart or finish processing the flowchart.

On the other hand, if it is determined that a scene containing an electrocautery output value has been edited, the control unit 41 determines a handpiece to be used, based on the procedure name of "cholecystectomy" and the device (electrocautery) to be used in the scene (S63).

The control unit 41 sets the timing to display the reference material/page number to "upon occurrence of electrocautery handpiece error" (S64). The control unit 41 sets the reference material/page number describing how to deal with cholecystic handpiece output error for the scene based on the set details (S65) and finishes processing.

Figure 25:
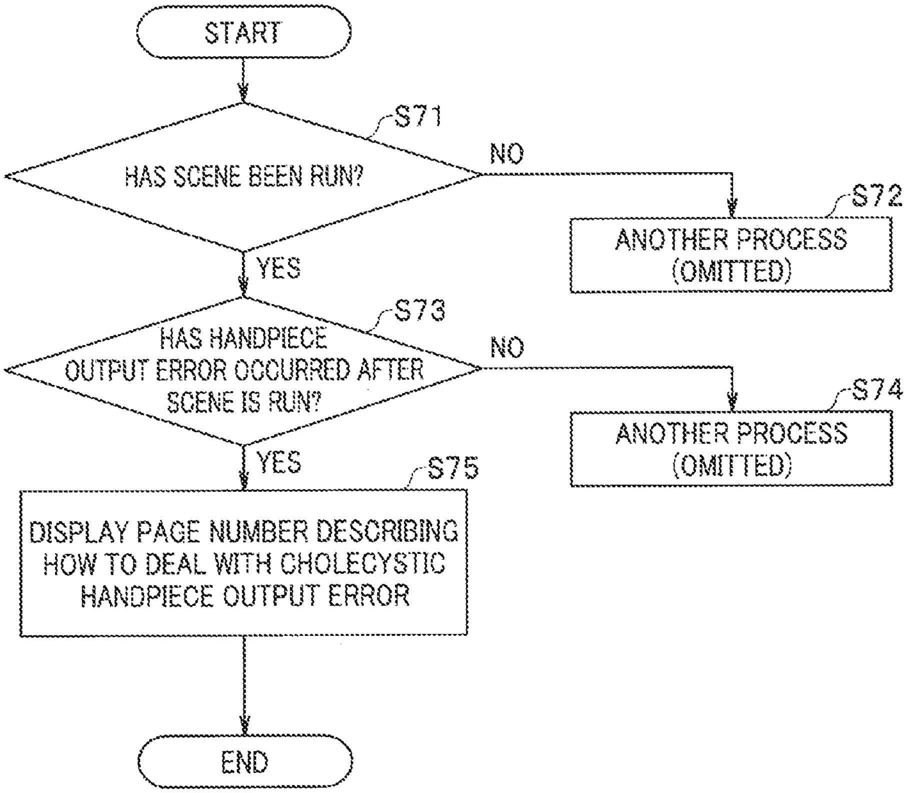
FIG. 25 is a flowchart showing a process flow of scene selection in an endoscope insertion scene of cholecystectomy procedures.

FIG. 25 is a flowchart showing a process flow of scene selection in an endoscope insertion scene of cholecystectomy procedures.

The control unit 41 determines whether the scene has been run (S71). If it is determined that the scene has not been run, the control unit 41 performs another process (S72). After performing the other process, the control unit 41 may either return to the first process of the flowchart or finish processing the flowchart.

On the other hand, if it is determined that the scene has been run, the control unit 41 determines whether a handpiece error has occurred after the scene is run (S73). If it is determined that no handpiece error has occurred after the scene is run, the control unit 41 performs another process (S74). After performing the other process, the control unit 41 may either return to the first process of the flowchart or finish processing the flowchart.

On the other hand, if it is determined that a handpiece error has occurred after the scene is run, the control unit 41 displays a page number describing how to deal with a cholecystic handpiece output error (S75) and finishes processing.

As described above, by setting, during scene selection, the page number of an instruction manual or timing to play a movie to "upon occurrence of error," the control unit 41 of the system controller 22 allows the user to check necessary information with a desired timing and deal with trouble quickly according to the progress of a surgical operation.

Note that in the flowcharts herein, by changing the execution sequence of individual steps, a plurality of steps may be carried out simultaneously or steps may be carried out with the sequence varied from run to run as long as the changes are not inconsistent with the nature of the procedures.

The present invention is not limited to the embodiments described above, and various changes, alterations and the like are possible without departing from the gist of the invention.

What is claimed is:

1. A control apparatus comprising:
a processor comprising hardware, wherein the processor is configured to:
select one scene of a plurality of scenes of a predetermined surgical operation based on user input;
change setting values of one or more connected devices of surgical apparatuses according to the scene selected;
select surgery-related information according to the scene selected;
determine whether the selected surgery-related information for the scene selected is information most frequently referred to in the scene based on a history of previously referenced surgery-related information for the scene selected stored in a storage device; and
display the information most frequently referred to on a display as the surgery-related information.

2. The control apparatus according to claim 1, wherein the processor is configured to select surgery-related information about the surgical apparatuses for which the setting values are changed.

3. The control apparatus according to claim 1, wherein the surgery-related information is a relevant part of a reference material that describes an operating procedure of the surgical apparatuses.

4. The control apparatus according to claim 3, wherein the surgery-related information is a chapter that represents a relevant part of a movie that shows the operating procedure of the surgical apparatuses.

5. The control apparatus according to claim 3, wherein display timing of the operating procedure of the surgical apparatuses is set in advance according to the scene selected.

6. The control apparatus according to claim 3, wherein the processor is configured to control display of the operating procedure by selecting a page number or a chapter of the reference material according to the scene selected.

7. The control apparatus according to claim 6, wherein the processor is configured to control display of the surgery-related information by selecting a page number or chapter of the reference material based on an order of the scene selected and a set value of a controlled device.

8. The control apparatus according to claim 1, wherein the processor is configured to:
discriminate display timing such that the surgery-related information is displayed on the display when a predetermined operation is performed; and
cause the display to display the surgery-related information according to the display timing discriminated.

9. The control apparatus according to claim 1, wherein the processor is configured to:
discriminate display timing such that the surgery-related information is displayed on the display when a predetermined error occurs; and
cause the display to display the surgery-related information according to the display timing discriminated.

10. The control apparatus according to claim 1, wherein the processor is further configured to:
determine whether the scene selected has been executed;
when the scene selected has been executed, determine whether the selected surgery-related information for the scene selected is information most frequently referred to in the scene;
when the selected surgery-related information for the scene selected is information most frequently referred to in the scene, display the information most frequently referred to on the display as the surgery-related information; and
when the selected surgery-related information for the scene selected is not information most frequently referred to in the scene, determine whether to output the information most frequently referred to.

11. A medical central control system comprising:
a plurality of medical devices including surgical apparatuses; and
a control apparatus that includes a processor comprising hardware, the processor being configured to control the plurality of medical devices,
wherein the processor is further configured to:
select one scene of a plurality of scenes of a predetermined surgical operation based on user input;
change setting values of one or more connected devices of surgical apparatuses according to the scene selected;
select surgery-related information according to the scene selected;
determine whether the selected surgery-related information for the scene selected is information most frequently referred to in the scene based on a history of previously referenced surgery-related information for the scene selected stored in a storage device; and
display the information most frequently referred to on a display as the surgery-related information.

12. The medical central control system according to claim 11, wherein the processor is configured to select surgery-related information about the surgical apparatuses for which the setting values are changed.

13. The medical central control system according to claim 11, wherein the surgery-related information is a relevant part of a reference material that describes an operating procedure of the surgical apparatuses.

14. The medical central control system according to claim 13, wherein the surgery-related information is a chapter that represents a relevant part of a movie that shows an operating procedure of the surgical apparatuses.

15. The medical central control system according to claim 11, wherein the processor is further configured to:

determine whether the scene selected has been executed;

when the scene selected has been executed, determine whether the selected surgery-related information for the scene selected is information most frequently referred to in the scene;

when the selected surgery-related information for the scene selected is information most frequently referred to in the scene, display the information most frequently referred to on the display as the surgery-related information; and when the selected surgery-related information for the scene selected is not information most frequently referred to in the scene, determine whether to output the information most frequently referred to.

16. A surgery-related information display method for a control apparatus including a processor comprising hardware, the processor being configured to control surgical apparatuses, the method comprising:

selecting one scene of a plurality of scenes of a predetermined surgical operation based on user input;

changing setting values of one or more connected devices of the surgical apparatuses according to the scene selected;

selecting surgery-related information according to the scene selected;

determining whether the selected surgery-related information for the scene selected is information most frequently referred to in the scene based on a history of previously referenced surgery-related information for the scene selected stored in a storage device; and displaying the information most frequently referred to on a display as the surgery-related information.

17. The surgery-related information display method according to claim 16, further comprising selecting surgery-related information about the surgical apparatuses for which the setting values are changed.

18. The surgery-related information display method according to claim 16, wherein the surgery-related information is a relevant part of a reference material that describes an operating procedure of the surgical apparatuses.

19. The surgery-related information display method according to claim 18, wherein the surgery-related information is a chapter that represents a relevant part of a movie that shows the operating procedure of the surgical apparatuses.

20. The surgery-related information display method according to claim 16, further comprising:

determining whether the scene selected has been executed;

when the scene selected has been executed, determining whether the selected surgery-related information for the scene selected is information most frequently referred to in the scene;

when the selected surgery-related information for the scene selected is information most frequently referred to in the scene, displaying the information most frequently referred to on the display as the surgery-related information; and when the selected surgery-related information for the scene selected is not information most frequently referred to in the scene, determining whether to output the information most frequently referred to.

* * * * *